(12) United States Patent  (10) Patent No.: US 8,119,978 B2
Islam et al.  (45) Date of Patent: Feb. 21, 2012

(54) APPARATUS AND METHODS FOR REAL-TIME VERIFICATION OF RADIATION THERAPY

(75) Inventors: Mohammad K. Islam, Oakville (CA); Bernhard D. Norrlinger, Mississauga (CA); Duncan M. Galbraith, Burlington (CA); David A. Jaffray, Etobicoke (CA); Robert K. Heaton, Toronto (CA); Jason Smale, Toronto (CA)

(73) Assignee: University Health Network, Toronto (CA)

( * ) Notice: Subject to any disclaimer, the term of this patent is extended or adjusted under 35 U.S.C. 154(b) by 69 days.

(21) Appl. No.: 12/373,159

(22) PCT Filed: Jul. 10, 2007

(86) PCT No.: PCT/CA2007/001209
§ 371 (c)(1),
(2), (4) Date: Sep. 25, 2009

(87) PCT Pub. No.: WO2008/006198
PCT Pub. Date: Dec. 17, 2008

(65) Prior Publication Data
US 2010/0012829 A1  Jan. 21, 2010

Related U.S. Application Data

(60) Provisional application No. 60/806,842, filed on Jul. 10, 2006.

(51) Int. Cl.
*G01D 18/00* (2006.01)
(52) U.S. Cl. ................................................ 250/252.1
(58) Field of Classification Search ................ 250/252.1
See application file for complete search history.

(56) References Cited

U.S. PATENT DOCUMENTS

| | | | | |
|---|---|---|---|---|
| 2,917,647 A * | 12/1959 | Landen et al. | ................. | 313/93 |
| 4,590,401 A * | 5/1986 | Goldstein et al. | ................. | 313/93 |
| 4,803,368 A * | 2/1989 | Barthelmes | ................. | 250/385.1 |
| 4,954,710 A | 9/1990 | Comparat et al. | | |
| 5,095,217 A | 3/1992 | Attix | | |
| 5,511,549 A * | 4/1996 | Legg et al. | ................. | 600/436 |
| 5,627,367 A | 5/1997 | Sofield | | |
| 6,714,620 B2 | 3/2004 | Caflisch et al. | | |
| 2004/0096033 A1* | 5/2004 | Seppi et al. | ................. | 378/65 |
| 2005/0056791 A1* | 3/2005 | Donaghue et al. | ................. | 250/394 |

FOREIGN PATENT DOCUMENTS

EP  0 838 844  4/1998

OTHER PUBLICATIONS

International Search Report/Written Opinion for corresponding PCT application No. PCT/CA2007/001209 date of mailing: Oct. 29, 2007.
International Preliminary Report on Patentability (IPRP) for corresponding PCT application No. PCT/CA2007/001209 date of issuance of the report: Jan. 13, 2009.
Poppe, B. et al. David—a translucent multi-wire transmission ionization chamber for in vivo verification of IMRT and conformal irradiation techniques, Institute of Physics Publishing, UK, Phys. Med. Biol. 51 (2006) 1237-1248, published Feb. 15, 2006.

* cited by examiner

*Primary Examiner* — Kiho Kim
(74) *Attorney, Agent, or Firm* — Bereskin & Parr LLP/S.E.N.C.R.L., s.r.l.

(57) ABSTRACT

Various embodiments are described herein for an area integrated fluence monitoring sensor that can be used to measure a radiation dose. The sensor comprises at least one Gradient Ion Chamber (GIC) comprising an ion chamber having a volume gradient across a length or width thereof, a gas or liquid located within the ion chamber and an electrode to detect ions generated within the gas or liquid when the at least one GIC is subjected to an ionizing radiation beam. Various embodiments are also described herein for an Integral Quality Monitoring system and associated method that can be used to measure and monitor the quality of radiation doses provided by a radiation treatment system.

53 Claims, 12 Drawing Sheets

APPARATUS AND METHODS FOR REAL-TIME VERIFICATION OF RADIATION THERAPY

CROSS REFERENCE TO RELATED APPLICATIONS

This is a national stage application of PCT/CA2007/001209 filed on Jul. 10, 2007 which claims priority from U.S. provisional application 60/806,842 filed on Jul. 10, 2006, both of which are incorporated herein by reference in their entirety.

FIELD

The embodiments described herein relate to the field of radiation treatment and in particular to a sensor and overall measurement and calculation methodologies that can be used for the real-time verification of the delivery of radiation dose.

BACKGROUND

The introduction of Intensity Modulated Radiation Therapy (IMRT) has revolutionized the field of radiation therapy. IMRT allows the delivery of highly conformal radiation treatment to well-defined target volumes while sparing the surrounding healthy tissue. However, there are many challenges associated with the proper execution of IMRT treatments. The process of intensity modulation in an IMRT field is accomplished through the delivery of many smaller beam segments by a sophisticated method, which synchronizes the production of the radiation beam with the dynamic motion of a Multileaf Collimator (MLC) assembly. The MLC assembly has several metal strips, referred to as fingers or leaves, which are used to shape the radiation beam. Accurate delivery of radiation dose and precise positioning of the leaves of the MLC assembly is essential. Small deviations from the intended energy fluence pattern of the beam segments can have much greater consequences to the patient treatment outcome compared to similar errors in other forms of radiation therapy.

Additionally, the workflow of modern radiation therapy involves a sophisticated network of software modules, hardware systems and the interaction of many multidisciplinary healthcare professionals. To ensure that the planned IMRT treatment is delivered as intended, great efforts are required, involving costly staff and machine time, to perform Quality Assurance (QA) tests. Current standard practice for IMRT patient plan QA involves a fragmented approach developed from QA procedures traditionally used for standard radiotherapy treatments, including: 1) planned dose verification through an ion chamber point dose measurement (requiring time on a treatment machine), or through the use of a secondary dose calculation software tool; 2) verification of beam fluence using either film or an electronic portal imaging device, both of which also require time on a treatment machine; and 3) manual checks of patient field parameters entered into a Record-and-Verify (R&V) system.

The need for time on a treatment machine to perform some or all of these QA procedures is costly in terms of staffing and infrastructure resources since either time must be scheduled on the machine during the normal treatment day, resulting in less time available for patient treatment, or the QA must be performed by staff outside of normal working hours. As well, QA of the IMRT patient plan and delivery system is typically performed prior to the first treatment session only. During the actual treatment sessions, which consists of 30 to 40 daily fractions, the control system of the treatment machine and the R&V system are relied upon to accurately deliver the treatment. However, after the initial pre-treatment QA, no independent checks are performed to ensure that the treatments are being delivered as intended, and so treatment errors introduced in subsequent sessions can go undetected. Common mistreatment scenarios can involve human errors as well as software and hardware malfunctions. For instance, the built-in radiation monitoring systems that are integrated into the treatment machine do not provide information of the radiation conditions following the final beam shaping devices, and so are insensitive to the MLC assembly and associated potential errors. In addition, leaf position sensors for the MLC assembly are not independent of the treatment machine and software, and therefore cannot detect all errors reliably. The current practice of IMRT is therefore vulnerable to errors and may lead to treatment incidences. However, up to now, there is no integrated, comprehensive QA solution that is available to meet the complexities associated with modern radiation therapy processes to provide workflow efficiency and integrated on-line treatment verification.

SUMMARY

In one aspect, at least one of the embodiments described herein provides an area integrated fluence monitoring sensor for measuring a radiation dose. The sensor comprises at least one Gradient Ion Chamber (GIC) comprising an ion chamber having a volume gradient across a length or width thereof; a gas or liquid located within the ion chamber; and an electrode to detect ions generated within the gas or liquid when the at least one GIC is subjected to an ionizing radiation beam.

In at least some cases, the volume gradient has a shape that generally monotonically increases in a given direction.

In at least some cases, the ion chamber is defined by electrodes and sidewalls that collectively provide a wedge shape.

In at least some cases, the at least one GIC further comprises a pair of polarizing electrodes defining upper and lower portions of the ion chamber and providing a portion of a housing for the at least one GIC, the pair of polarizing electrodes being oriented with respect to one another to provide the volume gradient; a pair of insulator regions separating end portions of the polarizing electrodes from one another at opposite ends of the ion chamber; and a pair of guard electrodes located within the insulating portions and configured to reduce the effect of leakage current on radiation dose measurement.

In at least some cases, the electrode that detects ions is a collector plate disposed between the pair of polarizing electrodes, each of the ends of the collector plate being located within one of the guard electrodes and the sensor further comprising an additional pair of insulator regions located within the guard electrodes to insulate the collector electrode from the guard electrodes.

Alternatively, the at least one GIC further comprises a polarizing electrode defining an upper or lower portion of the ion chamber and providing a portion of a housing for the at least one GIC; a collector plate disposed across from the polarizing electrode to define the volume gradient; insulator regions separating end portions of the polarizing electrode from the collector plate at opposite ends of the ion chamber; and a pair of guard electrodes located within the insulating portions and configured to reduce the effect of leakage current on radiation dose measurement.

The ion chamber generally has a surface area larger than the cross-sectional area of the ionizing radiation beam within the GIC.

In at least some cases, during use, the pair of polarizing electrodes are maintained at a potential difference in the range of 300 to 500 Volts.

In at least some cases, the gas is air and the ion chamber is at room pressure. Alternatively, the ion chamber can be pressurized.

In at least some cases, the sensor can further comprise a temperature sensor for performing temperature compensation on the radiation dose measurement and/or a pressure sensor for performing pressure compensation on the radiation therapy dose measurement.

In at least some cases, the sensor comprises first and second GICs, the first GIC having a first ion chamber with a first volume gradient and the second GIC having a second ion chamber with a second volume gradient, wherein the second volume gradient is perpendicular to the first volume gradient.

In at least some cases, the sensor comprises first and second GICs, the first GIC having a first ion chamber with a first volume gradient and the second GIC having a second ion chamber with a second volume gradient, wherein the second volume gradient is parallel to and in an opposite direction with respect to the first volume gradient.

In at least some cases with the parallel and opposite direction GICs, the sensor further comprises third and fourth GICs, the third GIC having a third ion chamber with a third volume gradient and the fourth GIC having a fourth ion chamber with a fourth volume gradient, wherein the fourth volume gradient is parallel to and in an opposite direction with respect to the third volume gradient and the first and second volume gradients are orthogonal with respect to the third and fourth volume gradients.

In another aspect, at least one of the embodiments described herein provides an integral Quality Monitoring (IQM) system for measuring a radiation dose provided by a radiation treatment system. The radiation treatment system establishes treatment parameters and includes a radiation source for generating radiation therapy according to the treatment parameters. The IQM system comprises an Area Integrated Fluence Monitoring Sensor (AIMS) including at least one Gradient Ion Chamber (GIC) comprising an ion chamber having a volume gradient and a gas or liquid, the at least one GIC being configured to provide a GIC signal containing information on radiation dose and location of the radiation dose based on ions generated within the ion chamber when subjected to an ionizing radiation beam, wherein the IQM system is configured to use the GIC signal, the treatment parameters, and the configuration of the radiation source to monitor characteristics of the radiation dose.

The IQM system further comprises an electrometer coupled to the AIMS for reading the GIC signal and providing measured AIMS signal data; and an IQM calculation module configured to predict expected AIMS signal data based on the treatment parameters, and the configuration of the radiation source. The IQM system is configured to generate actual AIMS signal data from the measured AIMS signal data and compare the expected AIMS signal data with the actual AIMS signal data to monitor the characteristics of the radiation dose.

The radiation source generally further comprises a Multileaf Collimator (MLC) assembly to shape the output of the radiation source and the GIC is positioned between the MLC assembly and a location where a patient is situated during radiation therapy.

In at least some cases, the AIMS comprises two or more GICs with ion chambers positioned to provide a multidirectional volume gradient, wherein the volume gradients of the ion chambers are in an orthogonal or in a parallel and opposite orientation with respect to one another.

In at least some cases, the electrometer is a wide dynamic range electrometer comprising two electrometers in a switchable dual configuration and a processor, wherein the processor is configured to switch between the electrometers to prevent saturation of the electrometers such that one of the electrometers is integrating the GIC signal and the other electrometer is in reset mode.

The processor can be configured to apply a gain correction factor to the output of the electrometers and to cumulatively add the outputs of the electrometers when switching between the electrometers while the radiation source is operating according to the treatment parameters.

In at least some cases, the outputs from the electrometers are re-scaled based on actual delivered centi-Monitor Unit (cMU) if the radiation source provides a cMU count.

In at least some cases, one of the electrometers comprises an integrator configured to integrate the GIC signal; an analog to digital converter configured to digitize the integrated GIC signal; and a logic gate configured to indicate a near saturation condition for of the integrator.

The IQM calculation module is generally configured to predict the expected AIMS signal data based on a model that includes a primary beam component that is radiated through a first area defined by the aperture formed by the MLC assembly and a leakage component radiated through a second area defined by jaws of the radiation source minus the first area.

Accordingly, the IQM calculation module can be configured to predict the expected AIMS signal data according to $$S = MU \cdot K \cdot ROF(X, Y) \left[ \int_{A_1} F(x, y)\sigma(x, y)dxdy + \int_{A-A_1} T(x, y)F(x, y)\sigma(x, y)dxdy \right]$$

where S is a total integrated signal produced by the at least one GIC, A is the area enclosed by the jaws of the MLC assembly, $A_1$ is the area created by the aperture of the MLC assembly, MU is a scalar dose delivered in Monitor Units, K is a constant of proportionality, ROF(X,Y) is a field-size dependent relative output factor, F(x,y) is a beam fluence produced by the linac (over Area $A_1$), $\sigma(x,y)$ is a chamber response function, and T(x,y) is an MLC transmission and leakage factor through the leaves of the MLC assembly (over Area $A-A_1$).

The IQM system is generally configured to provide radiation fluence measurements in real-time, and can further comprise data storage means to store measured and calculated radiation doses for given radiation treatment protocols.

In yet another aspect, at least one of the embodiments described herein provides a method for radiation dose measurement for a radiation treatment system. The radiation treatment system establishes treatment parameters and includes a radiation source for generating a radiation beam according to the treatment parameters. The method comprises:

positioning an Area Integrated Fluence Monitoring Sensor (AIMS) between the radiation source and a patient location, the AIMS including at least one Gradient Ion Chamber (GIC) comprising an ion chamber having a volume gradient and a gas or liquid;

predicting expected AIMS signal data based on the treatment parameters, the configuration of the radiation source and the AIMS;

operating the radiation source;

measuring AIMS signal data from the at least one GIC while the at least one GIC is subject to ionizing radiation;

generating actual AIMS signal data from the measured AIMS signal data and comparing the actual AIMS signal data with the expected AIMS signal data; and detecting errors in the treatment parameters and stopping treatment if the difference between the actual AIMS signal data and the expected AIMS signal data is not within tolerance limits.

The method is performed before, during or after radiation treatment.

In at least some cases, the method can include providing an indication to a user of the radiation treatment system when the difference between the actual AIMS signal data and the expected AIMS signal data is not within the tolerance limits.

In at least some cases, the method can include identifying a radiation treatment system setting error based on the comparison of the actual AIMS signal data with the expected AIMS signal data.

The radiation treatment system can be based on standard radiation therapy modes, an Intensity Modulated Radiation Therapy (IMRT) and/or an Image Guide Adaptive Radiotherapy (IGART).

The method can include performing the various types of functions outlined above for the IQM system. The method and the IQM system can also include using a GIC as defined above.

BRIEF DESCRIPTION OF THE DRAWINGS

For a better understanding of the various embodiments described herein and to show more clearly how they may be carried into effect, reference will now be made, by way of example only, to the accompanying drawings in which.

DETAILED DESCRIPTION OF THE EMBODIMENTS

Figure 1:
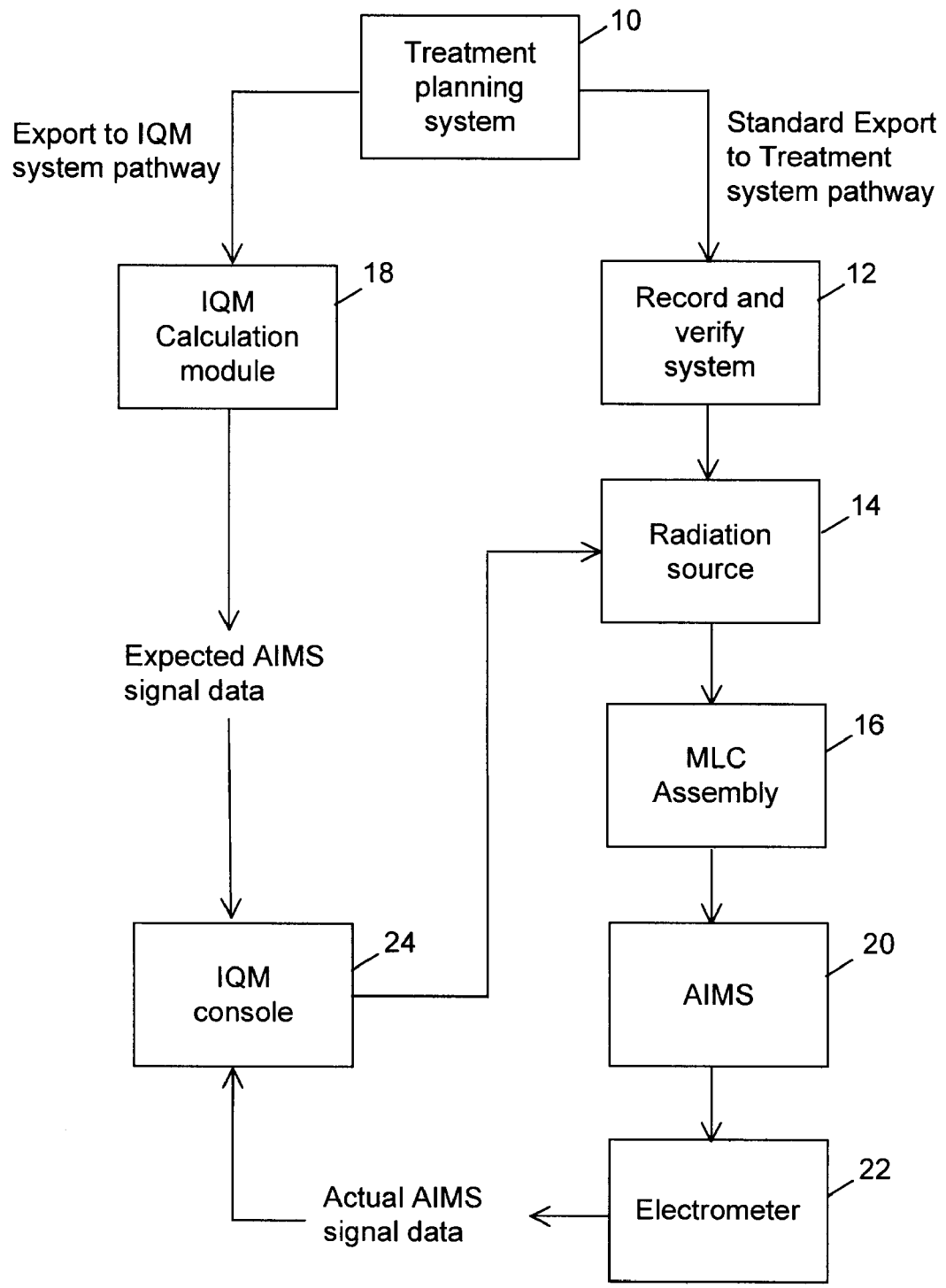
FIG. 1 is an illustration showing the components of an exemplary embodiment of an Integral Quality Monitor (IQM) system along with radiation treatment components.

It will be appreciated that for simplicity and clarity of illustration, elements shown in the figures have not necessarily been drawn to scale. Further, where considered appropriate, reference numerals may be repeated among the figures to indicate corresponding or analogous elements. In addition, numerous specific details are set forth in order to provide an adequate understanding for practicing the various embodiments described herein. However, it will be understood by those of ordinary skill in the art that the various embodiments described herein may be practiced without these specific details. In other instances, some methods, procedures and components have not been described in detail since they are well known to those skilled in the art.

In the context of dynamic IMRT and on-line Image Guided Adaptive Radiotherapy (IGART) treatment, an independent dose monitoring system is proposed herein that is positioned after the final beam-modifying device and can be used for safe treatment delivery. An integral quality monitoring (IQM) system, various embodiments of which are described herein, can be used as the independent dose monitoring system. Since the IQM system can perform, but is not limited to, radiation dosimetry monitoring tasks pertinent to both patient specific and delivery system QA, the implementation of the IQM system will eliminate a number of patient specific QA procedures and supplement delivery system QA needs in the rapidly evolving radiation therapy environment.

The IQM system described herein is a real-time treatment verification system, which can automatically and independently, without relying on the machine control system or R&V system, verify the accuracy of intensity modulated treatment for each and every treatment beam daily. The IQM system directly validates the accuracy of treatment delivery by comparing actual treatment data obtained by the AIMS with the treatment plan data in real time. The IQM system can also be utilized to perform the pre-treatment QA of complex treatment plans as well as a number of machine QA functions more efficiently. The IQM system offers a low cost, independent, and comprehensive real-time monitoring of treatment verification accuracy. The IQM system can also aid in the implementation of on-line IGART or any other on-line patient field planning/adjustment methodologies. Furthermore, through the use of the advanced imaging modalities that are now available, patient treatment plans can be created or modified based on daily changes in patient anatomy and position. During the delivery of the modified plan, the IQM system can provide real-time feedback that the plan is being delivered as intended.

The IQM system is stable and sufficiently sensitive to probable error conditions during the execution of high precision (e.g. IMRT) treatment delivery. Error conditions in treatment delivery may arise from: MLC leaf calibration error, MLC motor malfunction, incorrect field selection, incorrect wedge (orientation or angle), out-of-tolerance machine output, selection of wrong energy and Monitor Units (MU). The IQM system includes a large area radiation fluence monitor, mounted below the MLC assembly, and is able to verify the accuracy of treatment delivery and capture common error conditions. The IQM system can also verify IMRT fields while permitting the unperturbed transmission of the radiation intensity pattern to the patient. The IQM system increases treatment efficiencies compared to existing IMRT processes and fulfills a critical need required to advance the use of on-line IGART. The IQM system can increase patient throughput while enhancing patient safety in a cost effective manner.

Referring now to FIG. 1, shown therein is an illustration of the components of an exemplary embodiment of the IQM system along with radiation treatment system components. The radiation treatment system components include a treatment planning system 10, an R&V system 12, and a radiation source 14 having an MLC assembly 16. The radiation source 14 can be a linear accelerator or generally any other type of radiation generating source that is external to the patient. The IQM system components includes an IQM calculation module 18, an Area Integrated Fluence Monitoring sensor (AIMS) 20, an electrometer 22 and an IQM console 24. It should be noted that in alternative embodiments, at least two of the treatment planning system 10, the R&V system 12, the IQM calculation module 18 and the IQM console 22 can be provided by the same computing platform. In addition, in at least some cases, the IQM calculation module 18 and the IQM console 24 can be implemented using the same computing platform.

A patient plan is created by the treatment planning system 10 (TPS) and is then exported to two separate pathways: the standard export to treatment system pathway and the export to IQM system pathway. The standard export to treatment system pathway provides the treatment parameters to the R&V system 12 and the radiation source 14 (both otherwise known as the treatment delivery system). These parameters are used for the actual generation and delivery of the treatment. The export to IQM system pathway is a separate, independent export path of the same treatment data to the IQM system components. From this exported data, the IQM calculation module 18 predicts signals from the AIMS 20 based upon the radiation field segment data provided by the treatment planning system 10 and stores the predicted data as expected AIMS signal data. The operation of the IQM calculation module 18 can be automatic since no user intervention is required once the input parameters are provided by the treatment planning system 10. The IQM console 22 tracks the measured AIMS signal data from the AIMS 20, performs certain calculations (described below) to generate actual AIMS signal data and compares the actual AIMS signal data with the corresponding predicted AIMS signal data to verify the treatment delivery in real-time. The IQM console 22 can provide feedback or control data to the treatment delivery system 14 depending on the comparison of the actual AIMS signal data with the expected AIMS signal data.

The operation of the IQM system components can be done before a patient treatment session or during a patient treatment session. During patient treatment, in the event that agreement between the expected and actual AIMS signal data is out of tolerance, the IQM console 24 will stop beam delivery through the activation of an interlock signal to the treatment delivery system (in this case the linear accelerator or linac 14). The IQM console 24 can also provide a user interface with a graphical depiction of the expected and actual AIMS data signals, which is described in more detail below, so that a user can visually monitor the operation of the radiation treatment system and make any required adjustments or terminate treatment.

The effect of the AIMS on the radiation beams in terms of attenuation, effect on beam energy, flatness, symmetry and surface dose is typically minimal. However depending on the nature of the components of the AIMS 20, i.e. thickness, geometry etc., the AIMS 20 can have some effect. If required these effects can be easily incorporated into the beam modeling of the treatment planning system 10. The beam attenuation factor can be incorporated into the dose calculation since the effect on beam energy, flatness and symmetry can be accurately measured during the beam commissioning and entered into the planning system. The change in surface dose, if any at all, can be taken into account during the treatment planning process.

The AIMS 20 comprises a single or multiple large-area spatially Gradient Ion chamber (GIC) that is mounted just below the MLC assembly 16 of the linear accelerator 14, i.e. the AIMS 20 is mounted in between the MLC assembly 16 and the patient (not shown). The MLC assembly 16 and the AIMS 20 can be used with other radiation sources. The AIMS 20 encodes spatial as well as energy fluence information into one or more outputs, depending on the number of GICs that are used, as is described in more detail below. Accordingly, during treatment delivery, the AIMS 20 produces a specific signal that is dependent on the radiation field intensity, location and shape.

Figure 2:
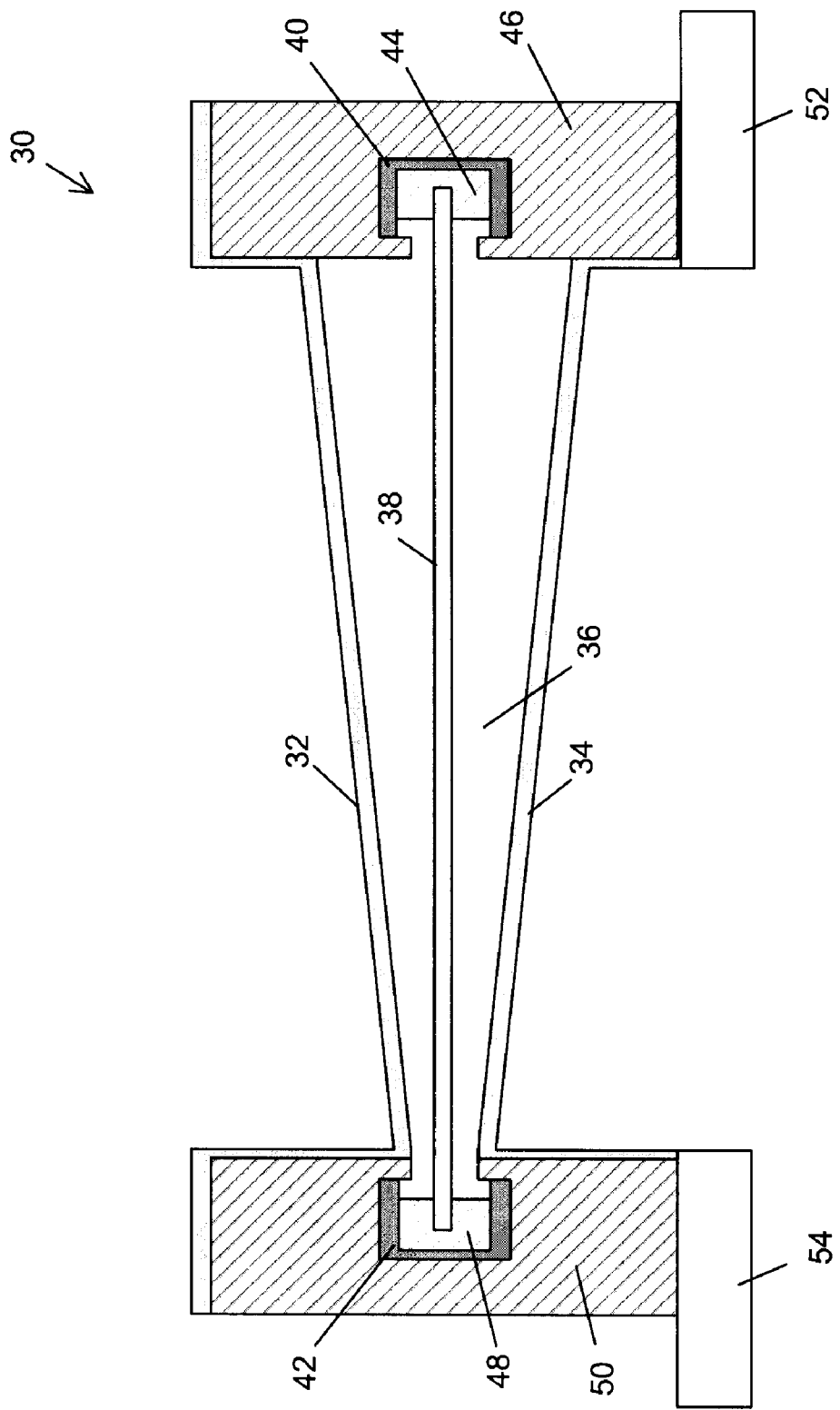
FIG. 2 is a cross-sectional view of an exemplary embodiment of a large area Gradient Sensitive Ion Chamber (GIC)

Referring now to FIG. 2, shown therein is a cross-sectional view of an exemplary embodiment of a GIC 30. The GIC 30 is a radiation fluence area detector, which can be utilized to determine the positional information of a beam segment in addition to verifying the integrated fluence-area-product. The GIC 30 can generate a signal pattern specific to any patient treatment field and is sensitive to small shifts/errors, on the order of millimeters, of a radiation beam segment. The GIC 30 also has no limiting effects on the beam characteristics, and has a negligible response to backscatter from the patient.

The GIC 30 includes polarizing electrodes 32 and 34 and sidewalls (not shown), which define an ion chamber 36 that contains an ionizable gas or liquid. The GIC 30 further includes a collector electrode 38, guard electrodes 40 and 42, insulator regions 44, 46, 48 and 50, and two base members 52 and 54. In at least some embodiments, the ionizable gas is air, which is at room temperature and at room pressure. Accordingly, the GIC 30 is unsealed so that the ion chamber 36 is maintained at room pressure. However, in other embodiments, the ion chamber 36 may be pressurized in order to obtain a larger ion signal during operation. In the former case the measurements can be compensated for pressure and temperature variation. Accordingly, there can be embodiments of the GIC that include pressure and temperature sensors where required. In addition, in alternative embodiments, a different gas other than air can be used, such as xenon gas and isooctane liquid. Based upon the actual air pressure and temperature, a compensation factor can be calculated, which takes into account the deviation of the mass of the ionizing air from its reference value, and this is applied to the measured AIMS signal(s). The fashion in which such a compensation factor is determined is known to those skilled in the art for conventional ion chambers and can similarly be applied to the ion chamber 36.

The ion chamber 36 exhibits a volume gradient thereby providing spatial sensitivity. The gradient in the chamber sensitivity, along with the direction of motion of the leaves of the MLC assembly 16, helps distinguish fields having the same fluence-area-product but different spatial configuration, and enables identification of probable error conditions such as MLC positioning error and incorrect field selection.

The volume of the ion chamber 36 in the present exemplary embodiment increases regularly from one side to the other. However, it will be appreciated that different geometries may be used and adapted for optimal detection of an area integrated fluence signal and variations/errors in the radiation beam fluence. In addition, the volume gradient of the ion chamber 36 need not be monotonic. To achieve a uniform gradient in response throughout, the separation between the plates at the edges may need to be nonlinear to account for the lateral loss of scattered electrons. In some cases, it may be possible to have an alternative embodiment in which the volume gradient in the active area of the ion chamber is characterized by a non-linear separation between the polarizing electrodes. In some cases, it may also be possible to have an alternative embodiment in which the ion chamber has a uniform gradient in the separation of the two polarizing electrodes in one direction and in an orthogonal direction have a staircase-type gradient thus offering a composite of a two-orthogonal GIC. Also, it will be appreciated that the volume gradient may be adapted to the desired radiation measurement. The magnitude of the volume gradient will depend upon the desired spatial sensitivity gradient. For example, if a one percent change in signal for a 2 mm shift in the aperture is desired, then the sensitivity of the chamber should change by the same rate. Therefore, this implies that the physical separation between the plates should change by the same spatial rate.

The polarizing electrodes 32 and 34 can be made using aluminum plates, although other conductive material can also be used as is known by those skilled in the art. Various values can be selected for the dimensions of the components of the GIC 30. For example, the thickness of the polarizing electrodes 32 and 34 can vary between 1 and 5 mm and can be 2 mm thick for example. Also continuing with this example, the polarizing electrodes can have a sensitive area of 22 cm×22 cm and the thickness of the ion chamber 36 can be between about 2 mm and 20 mm at the thin and thick ends respectively. The collector plate 38 can be a few millimeters thick. The base members 52 and 54 have a height of 6.5 mm. Continuing with the example, the overall height of the GIC 30 is 47.5 mm (this dimension can vary). The distance between the inner edges of the two insulating portions 46 and 50 were 239 mm and the chamber volume is about 570 cm$^3$. A GIC with these dimensions is capable of monitoring a 34×34 cm$^2$ field size at the isocenter of the linear accelerator 14. However, it will be appreciated that the area of the ion chamber 36 can be selected differently so that it is commensurate with the size of the radiation beam used during treatment and the volume gradient can be adjusted to provide the desired spatial sensitivity. It should be noted that these dimensions are provided as an example and are not meant to limit the embodiments of the GIC described herein.

The guard electrodes 40 and 42 prevent leakage of currents between the polarizing electrodes 32 and 34 and also prevent leakage currents from contributing to the signal that is measured by the collector electrode 38. The collector electrode 38 and the guard electrodes 40 and 42 can be made from aluminum as well other suitable conductive material. The collector electrode 38 does not have to have the same surface area as the polarizing electrodes 32 and 34. The insulator regions 44, 46, 48 and 50 can be made from any suitable insulating material such as plastic. The base members 52 and 54 can be made from aluminum. The base members 52 and 54 mechanically couple the GIC 30 to a portion of the radiation source such as the collimator face plate.

During use, the guard electrodes 40 and 44 can be maintained at ground, the collector electrode 38 can be maintained at a virtual ground, and the potential between the polarizing electrodes 32 and 34 can be in the range of 200 to 1,000 V, with a preferable operating potential difference in the range of 300 to 500 V. Alternatively, in other embodiments, the polarizing plates 32 and 34 may be at a virtual ground and the collector 38 at 200 to 1,000 volts. Due to the large surface area of the polarizing electrodes 32 and 34, the collector electrode 38 generates a current on the order of micro-Amps. The potential difference creates an electric field to transport the ions that are generated during operation of the radiation beam to the collector electrode 38.

Alternatively, in other embodiments, only one polarizing electrodes 32 or 34, may be used along with the collector electrode 38. In this case the polarizing electrode that is used defines an upper or lower portion of the ion chamber 36 and provides a portion of a housing for the GIC. The collector plate disposed across from the polarizing electrode in such a manner as to define the volume gradient; for example, the collector plate and the polarizing electrode can be disposed to define one half of the ion chamber 36 shown in FIG. 2. Insulator regions can also be used that separate end portions of the polarizing electrode from the collector plate at opposite ends of the ion chamber, and a pair of guard electrodes can be located within the insulating portions to reduce the effect of leakage current on radiation dose measurement.

It should be noted that in all of the embodiments described herein, the polarizing electrodes and the collector plate can have different shapes. For example, these elements have, but not limited to, a rectangular, square, circular or elliptical shape.

During operation, the gas in the ion chamber 36 is ionized due to exposure to the radiation beam from the radiation source 14. The rate of ionization is proportional to the intensity of the radiation beam and the volume of the ion chamber 36 (i.e. the location along the gradient of the GIC 30) that is being exposed to the radiation beam. The actual AIMS signal data measures the amount of ionization and therefore encodes the location and amount of ionizing radiation provided by the radiation source 14. The ion chamber 36 has a large surface area in order to capture the largest aperture of the MLC assembly 16. Therefore, the GIC 30 allows for the measurement of the overall radiation beam that is outputted from the combination of the MLC assembly 16 and the radiation source 14. The sensitivity in the measurement of the overall radiation beam depends on the slope of the gradient that is used as described previously.

Furthermore, since the radiation beams have an intensity that varies with location, since the leaves of the MLC assembly 16 are moved in and out of the field during operation, the output of the GIC 30 provides a unique signal with a temporal fingerprint. The shape of the radiation segment and the dwell time are reflected in the charge accumulation and time signature in the output of the GIC 30. In other words, with the gradient sensitivity of the GIC 30, the AIMS 20 has the capability of verifying both positional and shape information of individual radiation beam segments, through a single signal as the fingerprint of the treatment field. For instance, during an IMRT treatment session, the AIMS 20 generates temporal signals specific to the sequence of radiation beam segments, and these temporal signals can be compared in real-time with predicted values to verify the accuracy of treatment delivery since the sequence of radiation beam segments and associated apertures of the MLC assembly 16 are provided by the treatment planning system 10.

The GIC 30 described above can be used with the IQM system to validate radiation dose delivery accuracy and capture probable error conditions for the daily verification of IMRT treatment and pre-treatment IMRT quality assurance process. However, to enhance the sensitivity of the GIC 30 to the radiation beam delivery and to expand the IQM system's functionality to other possible error conditions, an AIMS having multiple GICs (also known as a stacked gradient chamber) can be used while maintaining control system simplicity and not affecting radiation beam quality. The other possible error conditions include: a combination of shift in position of the leaves of the MLC assembly 16 and expansion/contraction of the aperture of the MLC assembly 16, a lateral shift (orthogonal to the direction of MLC motion) in the aperture of the MLC assembly 16, or a mirrored aperture in the orthogonal direction to the motion of the MLC assembly 16 that can produce the same expected signal. An AIMS with multiple GICs can also be used in applications including: verification of on-line adjustment of field aperture location (arbitrary direction in the xy plane) for adaptation of patient positioning errors, identification of delivery error due to use of the wrong field, and change in machine output or beam asymmetry.

Figure 3A:
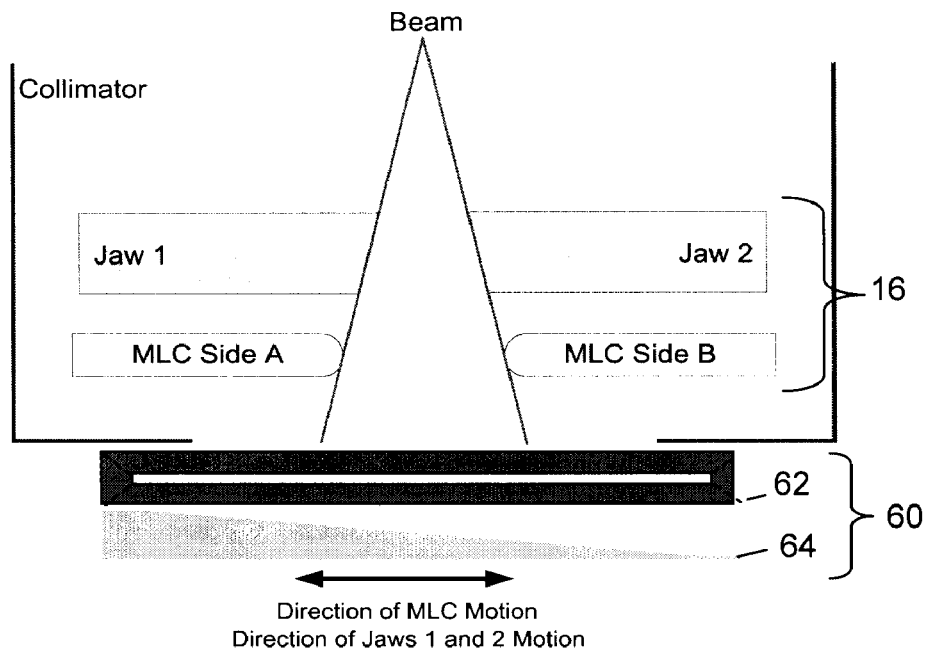
FIG. 3A is a schematic illustration of a portion of a radiation source and an MLC assembly along with an AIMS with two GICs having gradients orthogonally oriented with respect to one another.

Referring now to FIG. 3A, shown therein is a schematic illustration of a portion of the radiation source 14 and the MLC assembly 16 along with an AIMS 60 with two GICs 62 and 64 providing a stacked chamber configuration in which the gradients are orthogonally oriented with respect to one another. The GIC 62 can be considered to be shown in partial view (only the upper half is shown) and has a gradient in the direction of motion of the leaves and jaws of the MLC assembly 16. Alternatively, the GIC 62 can be considered to be an alternative embodiment which includes one polarizing electrode and one collector plate. The jaws may be part of the MLC assembly 16 or the collimator of the radiation source 14 depending on the manufacturer of these elements. The AIMS 60 can provide spatial sensitivity in both the X and Y directions and can be utilized to detect shifts in any direction. Accordingly, with this stacked chamber configuration, the IQM system can have the following additional features: the ability to capture error conditions due to a lateral (orthogonal to the MLC leaf motion direction) shift or mirrored aperture (with respect to MLC leaf motion direction) producing the same as the expected signal in a single GIC AIMS configuration. In addition, the IQM system enables the verification of an intentional shift in any arbitrary direction, composed of both X and Y directional shifts, of an aperture resulting from on-line IGART. Accordingly, an IQM system with the AIMS 60 can be utilized to detect and verify shifts introduced to a beam aperture during image guided on-line adaptive radiation therapy, in any direction.

Figure 3B:
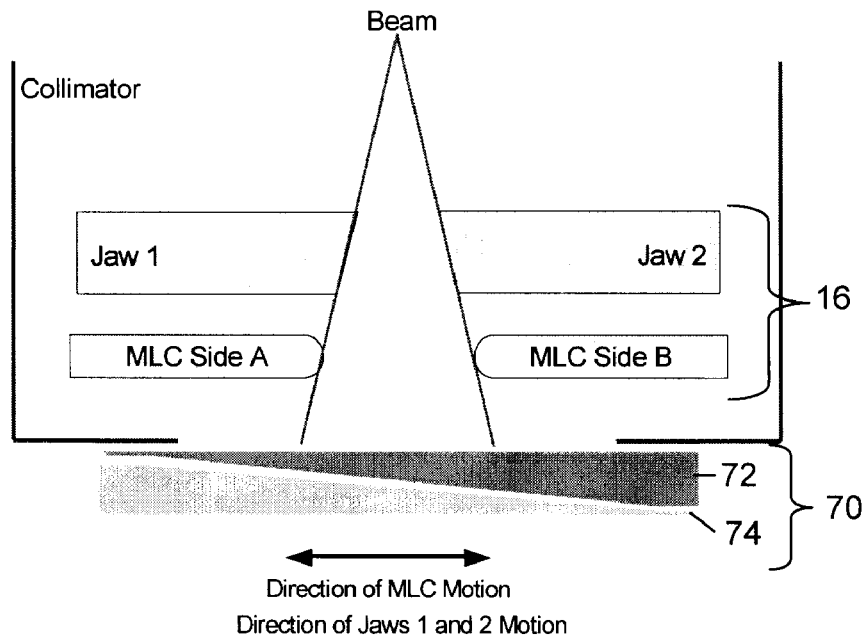
FIG. 3B is a schematic illustration of a portion of a radiation source and an MLC assembly along with an AIMS with two GICs having gradients oriented in a parallel and opposite direction with respect to one another.

Referring now to FIG. 3B, shown therein is a schematic illustration of a portion of the radiation source 14 and the MLC assembly 16 along with an AIMS 70 with two GICs 72 and 74 in a stacked chamber configuration in which the gradients are oriented in a parallel and opposite direction with respect to one another. The GICs 72 and 74 can be considered to be shown in partial view in which only the bottom and upper portions of the GICs 72 and 74 are shown. An example embodiment of the structure of an AIMS having a two-stacked chamber configuration with gradients in parallel and opposite directions is shown in FIG. 3D. Alternatively, the GICs 72 and 74 can be considered to be an alternative embodiment in which each GIC includes one polarizing plate and one collector plate. The signals from these two paired GICs 72 and 74 can be utilized to identify and diagnose some rare error conditions associated with treatment delivery that may go unnoticed with an IQM system having only a single GIC.

For example, the signal from a single GIC may be the same as that expected (i.e. a false positive) even if a larger (smaller) aperture is located at a position towards the thinner (thicker) direction of the gradient. This rare condition, may occur due to the selection of a wrong field, and can be easily identified with this stacked chamber configuration in which the GICs have their gradients oriented in a parallel but opposite direction to each other. In the case of a combination of a wrong aperture and shift, one GIC may yield a false positive signal but the other GIC will definitely yield an incorrect signal.

Figure 3C:
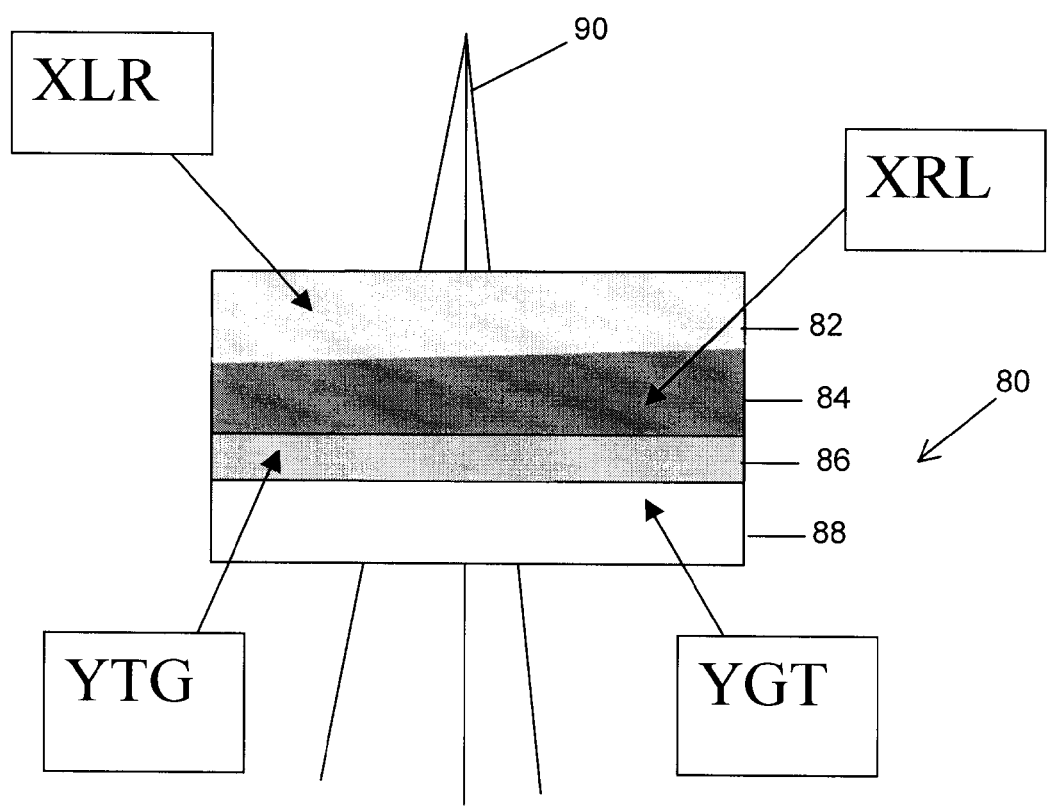
FIG. 3C is a schematic illustration of an AIMS having four GICs in a two-stacked chamber configuration.
Figure 3D:
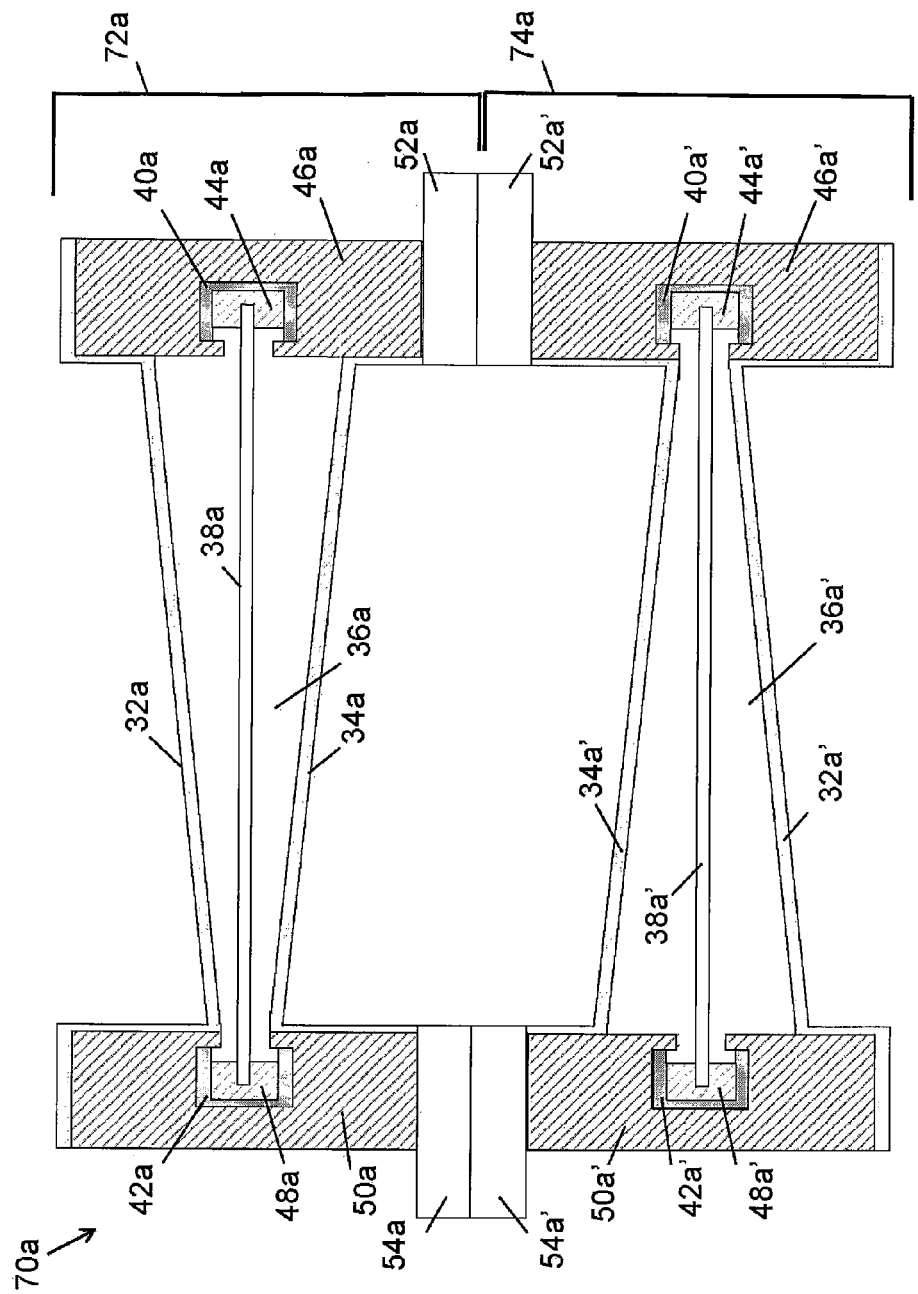
FIG. 3D is a cross-sectional view of an example embodiment of an AIMS having a two-stacked chamber configuration with gradients in parallel and opposite directions.

This capability can be built in both the X and Y directions by using an AIMS 80 having four GICs 82, 84, 86, and 88 in a two-stacked chamber configuration as is shown in FIG. 3C. A radiation beam 90 is also shown. The first stacked GIC includes a complementary pair of opposing GICs 82 and 84 with a unidirectional gradient, such as the combination shown in FIG. 3B. The second stacked GIC also includes a complementary pair that of opposing GICs 86 and 88 with a unidirectional gradient. However, the gradients of the first complementary pair (82,84) are orthogonal with the gradients of the second complementary pair (86, 88) in a configuration similar to that shown in FIG. 3A. The two orthogonal pairs of complementary GICs, spanning along and orthogonal to the leaf motion direction of the MLC assembly 16, can be utilized to decode spatial information of the radiation segments. The AIMS 80 can be used to identify aperture shifts in arbitrary directions. For example, a combination of shift and contraction/expansion of an aperture that would generate an acceptable signal in one GIC of a given pair may be out of tolerance in the complementary GIC of the pair. In addition to this robust error detection, the AIMS 80 facilitates enhanced diagnosis of the probable error conditions and enables the IQM system to perform some routine linear accelerator QA such as monitoring beam output, and symmetry checks. In order to perform routine beam output and symmetry QA, the same fixed field size and dose is delivered each time the QA is performed. The response of the IQM to this field will be known from the IQM Calculation module 18. The beam output measurement is the sum of the readings from all of the GICs. Beam symmetry is a measure of uniformity of beam intensity across a field. The beam intensity at a given distance from the central axis of the beam should be the same as all other points that are the same distance from the central axis of the field, i.e. a circle can be drawn with the center of the circle at the center of the beam, and all points on the circumference of the circle should have the same intensity, +/−2%. An asymmetry in the beam will result in a change in the beam intensity across some areas of the radiation field, which will be detected by a two orthogonal pairs configuration of GICs such as that shown in FIG. 3C.

In the various AIMS embodiments described above that include more than one GIC, multiple output signals are obtained (one from each GIC) which can be reviewed independently of one another. For example, Table 1 is a truth table that provides information on the output of the various GICs 82-88 shown in the AIMS 80. The GICs 82-88 are relabeled as XLR, XRL, YTG and YGT for the purposes of Table 1. The first letter identifies the stacked GIC pair and the next two letters designate the direction of the gradient. The letters T and G refer to the Target and Gun components of the accelerator, which are at opposite ends of the accelerating section, or gantry, of the accelerator. The letters T and G are used to refer to the directions of the radiation field that are in the same plane as the gantry, the radial plane. Accordingly, the T side of the field is closest to the target, and the G side is closest to the gun. The directions of the field that are orthogonal to the gantry, the transverse plane, are referred to as left and right. The X-pair GICs are orthogonal to the Y-pair GICs. Each pair includes GICs that are mirrored in gradient (i.e. have a unidirectional gradient). The leaf motion of the MLC assembly is along the X-direction. The truth table can be used for an AIMS having at least one GIC with an orientation that is covered by the truth table. The truth table can be implemented in the IQM software. Signals from all of the GIC's will be read by the IQM software. Any detected error in the expected versus calculated reading of any of the GIC's will result in a termination of beam delivery. However, utilizing the truth table, the IQM software will be able to report on the most likely cause of the error, aiding in troubleshooting.

TABLE 1

Truth Table for possible measurement errors for a multi-GIC AIMS

| Delivery Condition | Chamber Signals | | | | | |
|---|---|---|---|---|---|---|
| | XLR | XRL | YTG | YGT | XLR/XRL | YGT/YTG |
| Correct | √ | √ | √ | √ | √ | √ |
| 1: Shift in X | High/Low | Low/high | √ | √ | High/low | √ |
| 2: MLC malfunction | High/low | High/low | High/low | High/low | Out | Out |
| 3: Wrong Field | High/Low | Low/High | √ | √ | Out | √ |
| 3: Wrong Field | √ | √ | High/Low | Low/High | √ | Out |
| 3: Wrong Field | High/Low | Low/High | High/Low | Low/High | Out | Out |
| 4: Wrong Field | √ | Low/High | NA | NA | NA | NA |
| 5: MU or output or energy is Wrong | High/low | High/low | High/low | High/low | √ | √ |
| 6: For a fixed square field: Beam Symmetry error in X-direction | High/Low | Low/high | | | Out | |

The possible error scenarios that are listed in Table 1 include: (1) a shift of the field in the MLC direction due to MLC calibration error, (2) a wrong signal due to smaller/larger aperture due to a motor malfunction for one or a few MLC leaves, (3) a wrong field selection, (4) a rare situation in which one GIC can yield the expected AIMS signal due to a combination of wrong field and wrong position (this would be due to wrong field or patient selection), but the mirrored GIC does not produce the expected signal (identical conditions apply for the Y-direction as well), and (5) a wrong MU or Machine output or temperature & pressure sensor malfunction. The fifth scenario is applicable for routine machine QA. Identical conditions apply for beam symmetry error in the Y direction. Beam symmetry is measured and quoted in both planes of the radiation field, X, the left-right or transverse direction, and Y, the gun-target or radial direction. Accordingly, for the X direction, the XLR and XRL portions of the truth table are used and for the Y direction, the YTG and YGT portions of the truth table are used.

In summary, a single GIC-based IQM system in combination with supporting system QA tests can be utilized to effectively verify the accuracy of IMRT treatment delivery and flag errors but will not allow the identification of the cause of some errors. However, a multiple-GIC based system, on the other hand, providing multiple measured AIMS data signals, will allow for the verification of treatment delivery accuracy, diagnosis of some probable error conditions and performing some standard machine QA.

The output of a GIC is read by the electrometer 22. For a multi-GIC AIMS, one electrometer can be used for each GIC. Standard, commercially available electrometers are typically unable to integrate the charge from a large volume GIC without saturating. While it is possible to design an electrometer that can integrate a large charge, readout accuracy and resolution for low charge readings will generally be compromised and may not be acceptable for use with the IQM system. Accordingly, the electrometer 22 that is preferably used with the IQM is a Wide Dynamic Range Electrometer (WDE) that employs a design to overcome these aforementioned problems by using dual electrometers operating in a switching configuration.

Figure 4A:
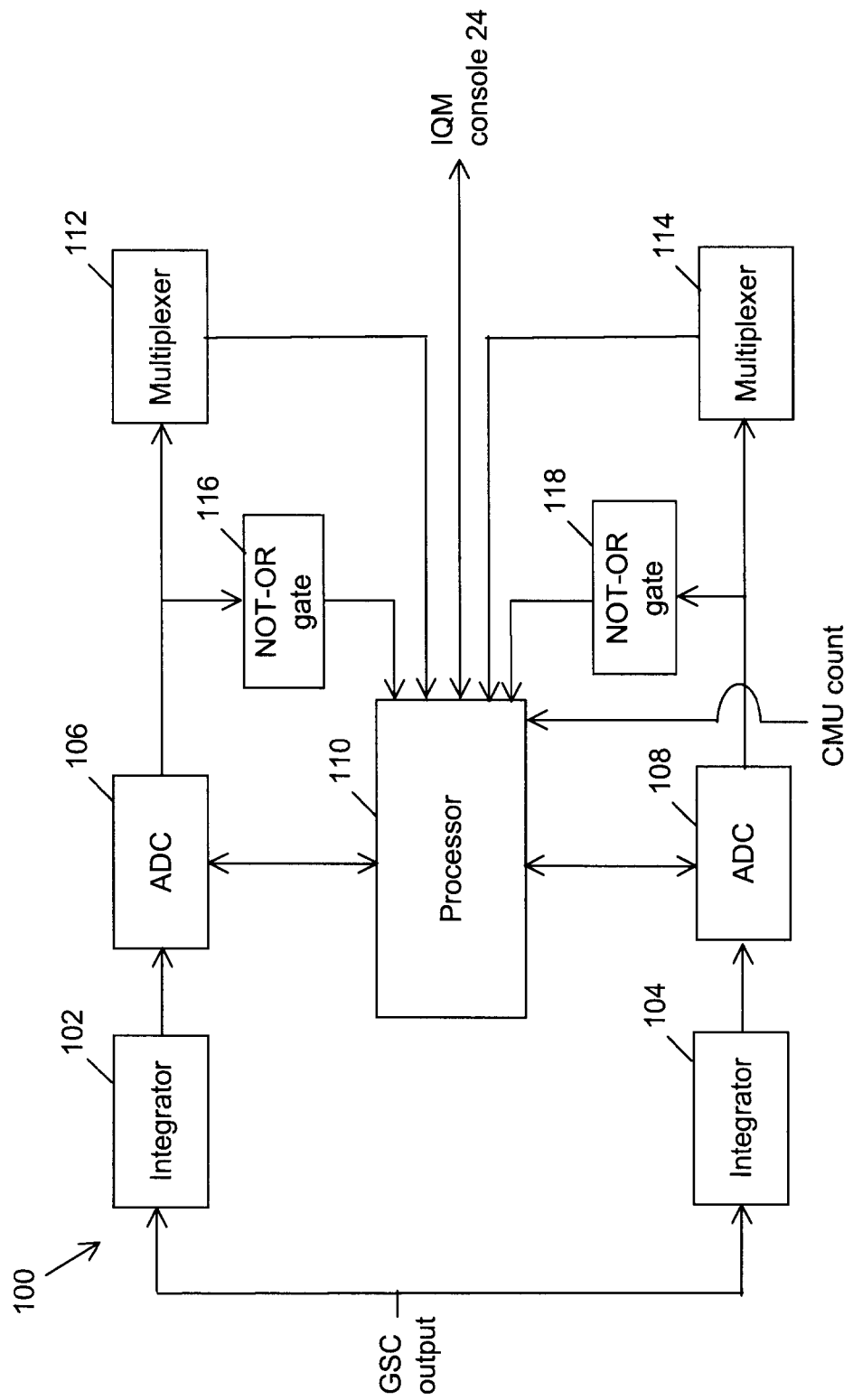
FIG. 4A is a block diagram of an electrometer that can be used to obtain charge readings from a GIC.

Referring now to FIG. 4A, shown therein is a block diagram of an exemplary embodiment of a WDE 100 that can be used to obtain charge readings from the AIMS 20. To measure the large charge from a large volume ionization chamber, the WDE 100 uses an automatic, switchable dual-integrator architecture. The electrometer 22 can integrate charge to an unlimited dynamic range without a significant loss of charge during the readout. The WDE 100 includes integrators 102 and 104, Analog to Digital Converters (ADCs) 106 and 108, a processor 110, multiplexers 112 and 114 and NOT-OR gates 116 and 118. In alternative embodiments, a single ADC with multiple input and output channels can be used. The processor 110 can be a microprocessor or a microcontroller.

The integrator 102, ADC 106 and multiplexer 112 can be considered to be a first electrometer and the integrator 104, ADC 108, and multiplexer 114 can be considered to be a second electrometer. Each integrator 102 and 104 utilizes an integrating capacitor type configuration. The integrating amplifiers 102 and 104 are commercially available integrated circuits that are designed specifically for use as an integrating electrometer, with on-chip reset, hold and multiplexing switches. The integrators 102 and 104 can be the ACF2101M op-amp circuit provided by Burr-Brown. The integrators 102 and 104 can utilize a high input resistance on the order of several Mega-Ohms and a feedback capacitor between the input and output pins on the order of one or more micro-Farads.

The outputs of the integrators 102 and 104 are digitized by the ADCs 106 and 108 and multiplexed by the multiplexers 112 and 114. In this exemplary embodiment, the ADCs 106 and 108 can be the ADS574 12-bit analog to digital converter provided by Texas Instruments. The multiplexers 112 and 114 are 16-bit digital multiplexers in which the first 12 bits are used, and the 4 higher order bits are tied to ground. The multiplexers 112 can be DM74150 multiplexers provided by Strong Exuberant Electronics.

The processor 110 controls the integrating channel multiplexing, charge readout and reset of the electrometers such that one electrometer is integrating the ion chamber signal while the output of the other electrometer is being processed. The processor 110 is also responsible for communication with the IQM console 24. The processor 110 can be a pic18f2550 microprocessor made by Microchip. Using this method, large charge measurements are possible while maintaining the accuracy and resolution of low charge measurements. The maximum measurable charge is limited only by the firmware employed by the processor 110. The reproducibility and linearity of the WDE design is comparable to commercially available electrometers, as shown below with respect to FIGS. 4B and 4C.

The output from a GIC is applied to both integrators 102 and 104 simultaneously, however only one integrator is allowed to charge while the other integrator is held in reset mode. Assuming the GIC is charging the integrator 102, the integrator 104 is held in reset. The output of the integrator 102 is continuously monitored via the ADC 106 and the associated NOT-OR gate 116. The ADC 106 converts the voltage output of the integrator 102 to a digital word or count. The three most significant bits of the digital word are applied to the NOT-OR gate 116 and when these three bits are all at a logic level of '0' (i.e. a low level), the integrator 102 is near saturation. The processor 110 detects this near saturation state and opens the reset switch of the integrator 104, which then begins to integrate the ion chamber current provided by the GIC. The processor 110 then reads the final value of the ADC 106 through the multiplexer 112, adds this value to a previous cumulative reading (if there is one), outputs this sum to the IQM console 24, and then applies the reset to the integrator 102. The process then continues using the integrator 104. The cycle continues as long as the GIC is producing current.

The firmware employed by the processor 110 applies appropriate processing to the outputs of the ADCs 106 and 108 to read the charge being produced by the GIC. To compensate for minor differences in the sensitivities of the integrators 102 and 104 (due mainly to differences in integrating capacitor values), a gain correction factor, determined experimentally and stored in the memory (not shown) of the processor 110, is applied to the values read from the ADCs 106 and 108. The processor 110 accumulates the corrected outputs of the ADCs 106 and 108 to produce a signal proportional to the total charge collected by the GIC, and provides the signal to the IQM console 24 which performs a further calculation, which is described below, to determine the actual AIMS signal data.

The output $E_{out}$ of the dual electrometer WDE 100 can be expressed as:

$$E_{out} = \text{ADCCount}_{Cum} + (\text{ADCx}_{counts} \times \text{ADCx}_{gain}) \quad (1)$$

where $\text{ADCCount}_{Cum}$ is the cumulative ADC count value from both ADCs 106 and 108, $\text{ADCx}_{counts}$ is the current count value from either ADC 106 or ADC 108, depending on which integrator 102 and 104 is operational, and $\text{ADCx}_{gain}$ is the corresponding gain correction value for ADC 106 or ADC 108. The output $E_{out}$ is further processed by the IQM console 24 to convert the total ADC counts to a value representing the measured fluence of the treatment field, i.e. the actual AIMS signal data (see the IQM calculations described below). The conversion is a re-scaling or re-normalization of the ADC counts. This is done by getting a reading from the AIMS for a standard reference field, likely a 100 MU, 10 cm×10 cm field, and then assigning a number to this value, such as say 100 for example. A scaling factor can then be calculated by:

$$F_{scaling} = 100/\text{Reading}_{Ref} \quad (2)$$

This scaling factor can then be used in subsequent readings to re-scale the AIMS output. Alternatively, this conversion can be done by the processor 110 as well.

The WDE 100 monitors the state of the radiation beam from the radiation source 14, and is able to detect when the radiation beam turns on and off, and the pause in the radiation beam during the MLC move segment of a step and shoot IMRT beam. When a segment pause is detected, the WDE 100 will output the current sum of the ADC counts as well as an S character to indicate to the IQM console 24 that a complete segment has been delivered.

As an option, the WDE 100 is able to accept as input the centi-Monitor Unit count (cMU count) from the radiation source 14 if this information is provided. In some models of linear accelerators, the actual number of cMUs delivered for a given field segment can differ significantly from the expected cMUs. The magnitude of this error is dependent on the expected cMU and the dose rate (MU/min). This MU delivery error is known and generally accepted, but is a problem for the IQM system because the IQM console 24 will calculate the expected signal based on the planned MU for the segment. Therefore, during treatment delivery the IQM will record an error in the measured versus the expected IQM readings if the actual number of cMUs that are delivered are not taken into account. The cMU count, which is available as a pulse signal from the linear accelerator, can be used by the IQM console 24 to re-scale the readings from the AIMS by the actual delivered cMU, allowing for better agreement between the measured and expected measurements.

Figure 4B:
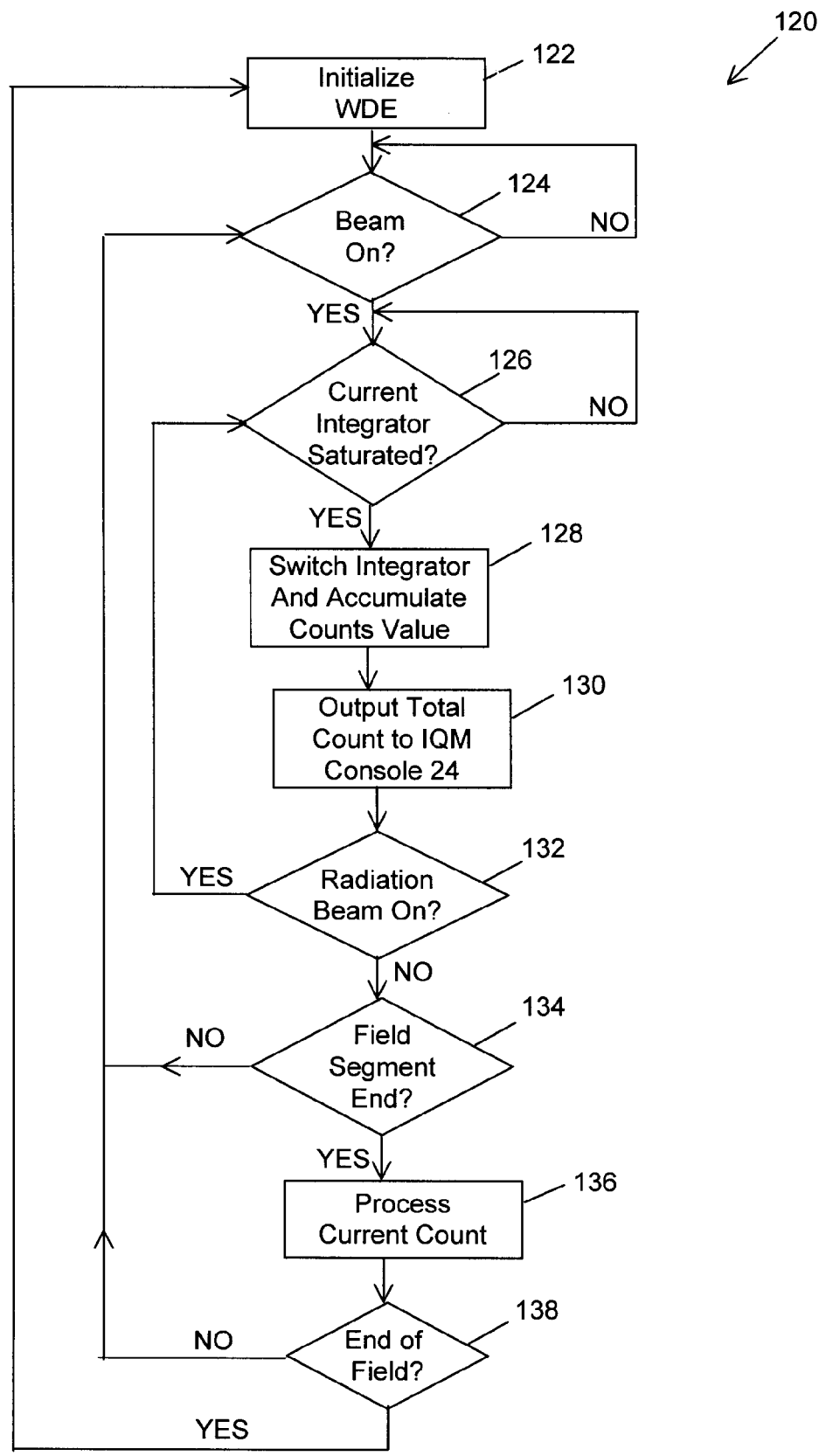
FIG. 4B is a flowchart diagram of an exemplary embodiment of a method for measuring charge from a GIC.

The operation of the WDE 100 during delivery of a treatment field in order to measure charge from the GIC is defined by method 120 shown in FIG. 4B. At step 122, the radiation beam is off, and the WDE 100 is initialized by setting the output of both integrators 102 and 104 to 0, setting the integrator 102 to integrate mode and the integrator 104 to reset mode (alternatively integrator 104 may be initialized to integrate mode and integrator 102 may be set to reset). The total counts is set to 0. The WDE 100 is in idle mode.

At step 124, the radiation beam is turned on. The processor 110 detects a "beam on" condition when a count of 3 is read from the ADC 106. At step 126, the processor 110 begins to monitor the output of the NOT-OR gate 116 to determine if the integrator 102 is saturated. It should be noted that this can be changed to monitoring the NOT-OR gate 118 to determine if the integrator 104 is saturated when the integrator 104 is enabled but this description will assume that integrator 102 is currently enabled. When the output of the NOT-OR gate 116 indicates that the integrator 102 is near saturation (for example the 3 most significant bits of the output of the ADC 106 are at a '0' level), the method 120 proceeds to step 128 at which point the processor 110 switches the integrator 104 to integrate mode, reads the counts from the ADC 106 and switches the integrator 102 to reset mode. The counts from the ADC 106 are gain-corrected and added to the cumulative total counts value.

At step 130, the cumulative total counts value is output to the IQM console 24. At step 132, the method 120 determines whether the radiation beam is still on and if so repeats steps 126 to 130 continuously, cycling between the integrators 102 and 104 as needed while the radiation beam is on. If the radiation beam is not on, the method 120 proceeds to step 134 at which point the method 120 determines whether a field segment end has occurred. The processor 110 can detect a field segment end if there is a pause in the radiation beam of at least 30 msec. If this is so, the method 120 proceeds to step 136 at which point the processor 110 will then process the current count from the ADC corresponding to the currently enabled integrator and output the total counts to the IQM console 24, followed by an 'S' character to signal the end of a segment. The cMU count will also be output if available (this is optional depending on the type of radiation source). The total counts is not reset to 0 since the accumulation of counts will continue if the radiation beam restarts.

At step 138, the method 120 monitors whether there is an end of field condition, which occurs when there is no signal from the GIC for at least 7 seconds. If this is true, the counts from the ADC corresponding to the currently enabled integrator are then processed and sent to the IQM console 24. The method 120 then goes to step 122 at which point the total counts and both integrators are reset to 0. The WDE 100 then returns to idle mode.

Careful component selection and layout of the components of the WDE 100 ensures that charge loss through leakage currents are kept to a minimum, i.e. approximately $0.783 \times 10^{-8}$ C over 5 minutes. This leakage current is removed during the beam-off period using an auto-reset function, in which the integrators 102 and 104 of the WDE 100 are continuously reset until a beam-on condition is detected. In addition, it has been found that the range of the WDE is approximately $0.05 \times 10^{-8}$ C to $2,237 \times 10^{-8}$ C. The upper limit is determined by the firmware employed by the processor 110 and can be increased if desired. The upper limit can be increased in firmware by increasing the number of bits allocated to the registers used to store the accumulated counts (i.e. by increase the amount of memory available to the accumulated count variable).

Figure 4C:
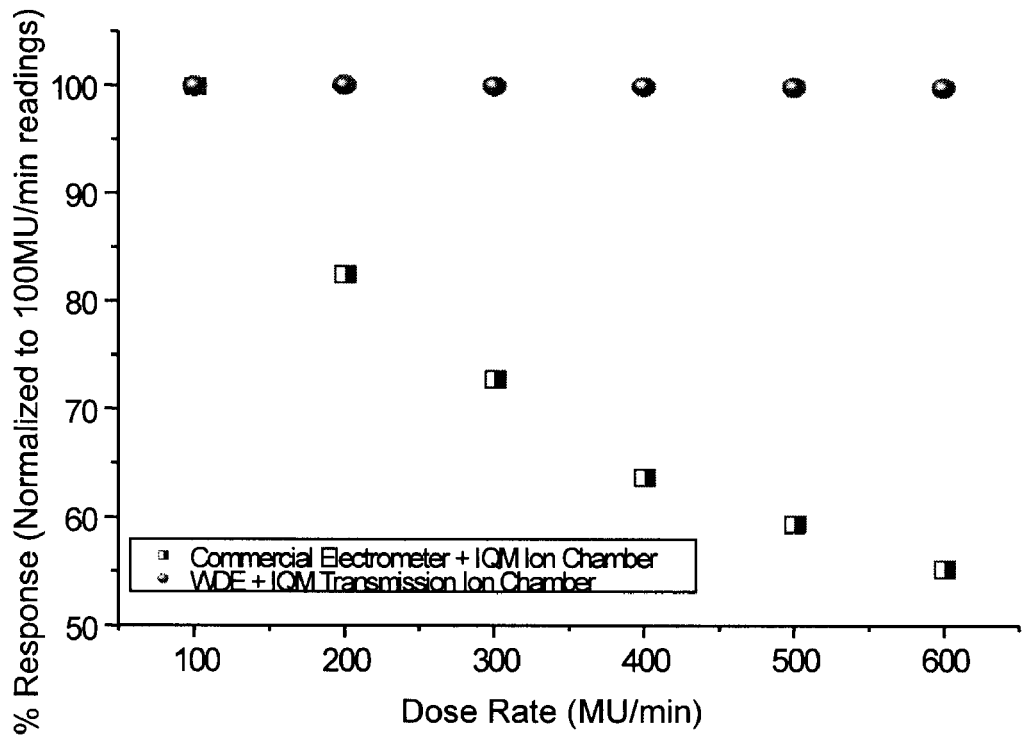
FIGS. 4C and 4D are graphs comparing the response of the electrometer of FIG. 4A with a standard commercially available electrometer.

For large ion chamber current measurements of 5 uA, the WDE 100 is able to measure the charge to within an accuracy of 2%, compared to a 45% error when using a commercial electrometer. This is shown in FIG. 4C in which the same total dose, and therefore total charge, was delivered to both the WDE 100 and a commercial electrometer (a Keithley 35040 Advanced Therapy Electrometer) at different dose rates. The current from the ion chamber increases as the dose rate increases. The electrometers should give the same reading regardless of dose rate. The commercial electrometer showed a significant loss of signal at a higher dose rate due to lost charge. The WDE 100 did not show a significant loss of charge.

Figure 4D:
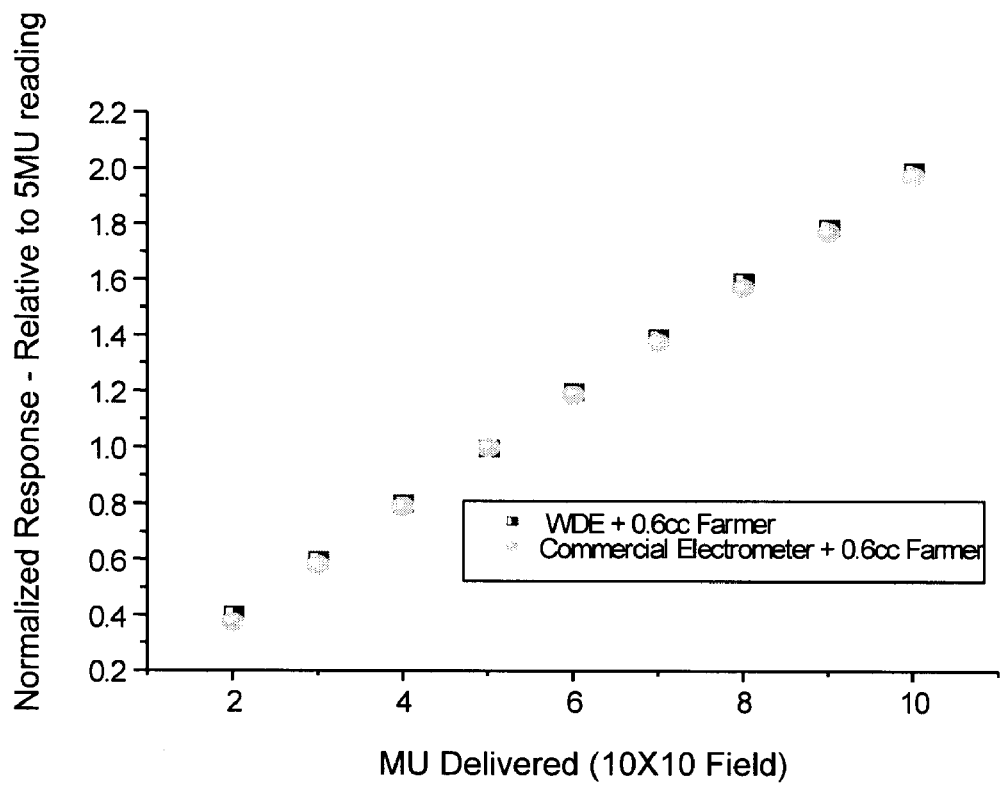

FIG. 4D shows a comparison of the linearity of readings from the WDE 100 and the commercial electrometer with respect to increasing dose. In this case, a standard 0.6 cc Farmer-type chamber was used to characterize the low current performance of the WDE 100. The linearity standard deviation is 0.007%, which is comparable to commercial electrometers.

The AIMS 20 has been characterized to produce a system response model that is used by the IQM calculation module 18 to provide a prediction of the output of the AIMS 20 based on the patient treatment plan. In conjunction with clinical treatment tolerances, the IQM console 24 compares the measured beam output (i.e. the actual AIMS signal data) to the expected output of the model (i.e. the expected AIMS signal data) in real-time to perform QA prior to a treatment session and during a treatment session.

Figure 5A:
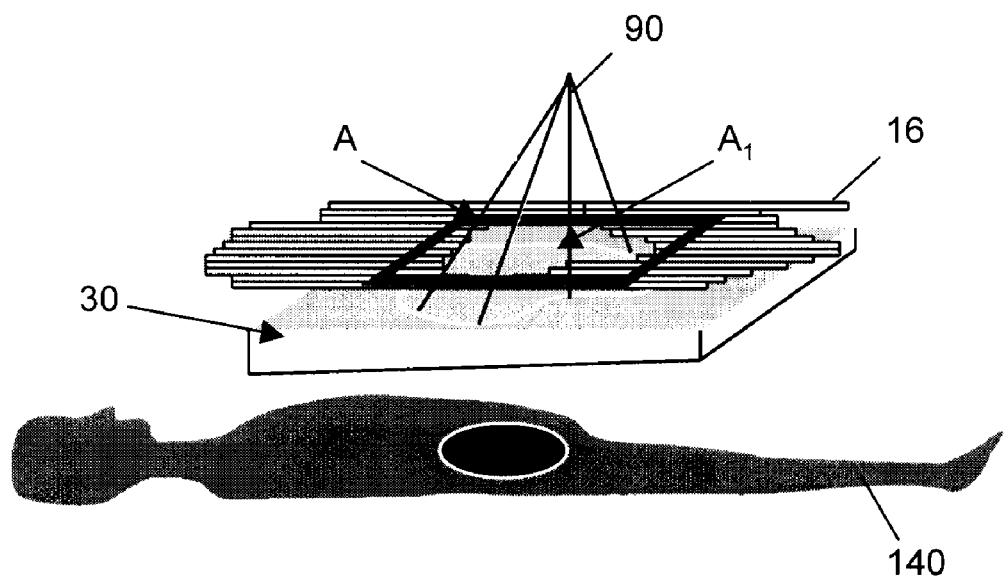
FIG. 5A is an illustration of geometry used in IQM calculation.

The proximity of the GIC 30 to the treatment head subjects it to an increased electron and scatter component compared to typical beam dosimetry performed at isocentre. The GIC 30 also has a plate separation gradient producing a non-uniform response profile, and the ion chamber 36 is larger than the radiation beam being measured, leading to electron equilibrium challenges. In addition, the beam fluence produced by the radiation source 14 varies over the entire field, including contributions from the primary beam through the aperture of the MLC assembly 16, transmission through the leaves of the MLC assembly 16, and transmission through the jaws of the MLC assembly 16. This geometry is shown in FIG. 5A which shows the radiation beam 90, the MLC assembly 16 with the MLC leaves defining an area $A_1$, a lower portion of the GIC 30 and a patient 120. Modeling the response of the GIC 30 to a clinical treatment plan when the GIC 30 is mounted close to the treatment head of the radiation source 14 requires taking these effects into consideration. An empirical approach has been taken in modeling the response of the GIC 30 by using a series of full-field and beamlet measurement data, while taking into account the MLC dosimetric parameters and the spatial response of the GIC 30.

Figure 5B:
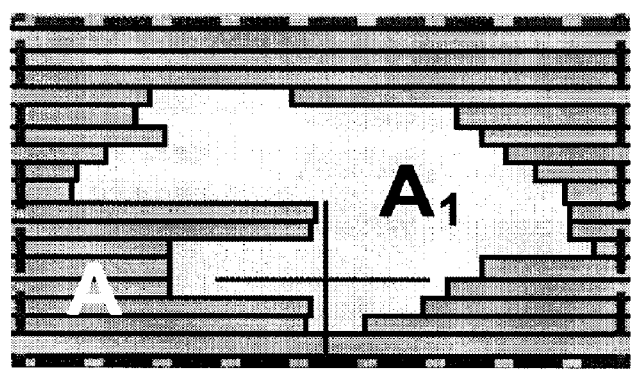
FIG. 5B is a top view of an MLC pattern illustrating areas A and $A_1$ used in IQM calculation.

The radiation fluence produced by the linac over the entire field can be separated into several main components: the primary beam component through the jaws and aperture of the MLC assembly 16, leakage and transmission through the MLC assembly 16, and the field size-dependent "relative output factor". The first two components are illustrated from a beam's eye view (BEV) in FIG. 5B. The field area A is defined by the jaw positions of the MLC assembly 16 and is shown as a dotted rectangular box. The leaves of the MLC assembly 16 create an aperture with area $A_1$, i.e. the primary beam component which is considered to be the signal of interest. The MLC assembly 16 shields the area $A-A_1$ within the jaw-defined aperture. The component of the signal due to leakage and leaf transmission over the area $A-A_1$ is the leakage component which is considered to be noise. The crosshairs illustrate the central axis of the field.

The primary beam component through the jaws and aperture of the MLC assembly 16, and the leakage and transmission through the MLC assembly 16 are modeled as components of the single integrated signal S from the GIC chamber 30 in equation 3:

$$S = MU \cdot K \cdot ROF(X, Y) \left[ \int_{A_1} F(x, y)\sigma(x, y)dxdy + \int_{A-A_1} T(x, y)F(x, y)\sigma(x, y)dxdy \right] \quad (3)$$

where S is the total integrated signal produced by the GIC 30, A is the area enclosed by the jaws of the MLC assembly 16, $A_1$ is the area created by the aperture of the MLC assembly 16, MU is the scalar dose delivered in Monitor Units, K is a constant of proportionality, ROF(X,Y) is a field-size dependent relative output factor, F(x,y) is a beam fluence produced by the linac (over Area $A_1$), σ(x,y) is a chamber response gradient, and T(x,y) is an MLC transmission and leakage factor through the leaves of the MLC assembly 16 (over Area $A-A_1$). The factors T(x,y) and σ(x,y) are determined experimentally, while the factor F(x,y) is provided by the treatment planning system. The coordinates X, Y refer to the jaw positions of the MLC assembly 16, while the coordinates x,y refer to specific coordinates over the area of integration. The integral term over area $A_1$ refers to the signal due to the primary beam aperture, while the second integral refers to the signal due to aggregate MLC leakage and other scatter components.

The constant of proportionality K is used to normalize the calculation result to measurement units equivalent to the output of the WDE 100, allowing for a direct comparison between the calculated and measured fluence values. The constant K is determined by obtaining the measured IQM fluence output per unit dose (MU) when irradiating the GIC 30 with a 10 cm×10 cm reference field, calculating the expected fluence value (with K=1.000) for the same field, and performing the calculation of equation 4.

$$K = S_{measured}/S_{calculated(k=1.00)} \quad (4)$$

The Monitor Units (MU) are the dose measurement units used by the linear accelerator. Linear accelerator dosimetry systems report delivered dose in MU, and patient fields are programmed to give a fixed number of MU. The actual dose value (as measured in cGy) of an MU is dependent on many factors, including field size (ROF), depth in water (tissue), distance from the source, etc., but is set such that 1 MU=1 cGy under a reference measurement condition, usually defined as the depth (in cm) of maximum dose in water (varies with beam energy) at a distance of 100 cm from the beam source with a field size of 10 cm×10 cm. The dose delivered by a linear accelerator varies with the field size defined by the collimator. This effect, called Relative Output Factor (ROF) is defined as:

$$ROF = D'_{jaws}(air)/D'_{ref}(air) \quad (5)$$

where: $D'_{jaws}(air)$ is the measured dose in air at a given field size and $D'_{ref}(air)$ is the measured dose in air at a reference field size, usually 10 cm×10 cm. The ROF is used to correct the MUs for the field size.

The first integral term indicates that the primary beam response consists of the beam fluence and GIC response over an area $A_1$ (x,y). The second integral term, the leakage response, has been modeled separately, consisting of the beam fluence, chamber response, and the transmission through the leaves of the MLC assembly 16. Both components will always be present for an IMRT patient treatment plan that uses the MLC assembly 16 to modulate beam intensity. Similarly, they will both contribute to the total response of the GIC. Instead of attempting to independently measure and model the terms F(x,y), σ(x,y), and T(x,y), the effects have been considered together in their respective integral terms. A mapping can be conducted using a series of measurements on the linac to account for these main sources of incident radiation on the GIC 30. The main assumption made by modeling the system in this way is that the integral of a series of elementary beamlets is equal, or roughly equal, to a single larger beam. This assumption is valid if the jaws (and therefore ROF) are kept constant during the mapping.

The spatial response function of the GIC can be determined by sequentially scanning a small pencil-beam aperture, defined by the MLC assembly, over the entire chamber area of the GIC, and making relative measurements, while taking into account the signal components due to the leakage and transmission through the leaves of the MLC assembly 16. The relative measurements can be obtained using a series of MLC defined apertures of increasing size. Incrementally increasing the aperture size of the MLC assembly 16 gives an estimate of the signal due to irradiation of that spatial area independent of leakage. In this case, a smaller aperture signal is subtracted from the larger aperture signal to give the response of the GIC 30 to the incremental aperture. This process is repeated until the response of the GIC is mapped. For these measurements the GIC is mounted at the collimator face (as will be used during clinical application) and the X and Y jaws are fixed at a large field size (e.g. 34 cm×34 cm with respect to the prototype GIC described above.)

To obtain the leakage map, the leaves of the MLC assembly 16 are closed to completely block the collimator opening. An image of the MLC transmission is obtained using film, which is then digitized, sampled and normalized to create an array of relative response numbers with 1.000 corresponding to the highest measured film response. A gradient correction, as measured by the primary response map, is then applied to the array, resulting in a map of the response of the GIC 30 to leakage through the MLC assembly 16.

Once the primary response and leakage maps have been created, they can be used for different MLC apertures and shapes over the entire field. Using sector integration, the response of the GIC to a given MLC defined field can be predicted through the summation of many small beamlets, using the primary response map in areas that are fully exposed to the beam, and accounting for leakage in areas that are within an area defined by the open jaws but shielded by the MLC assembly 16.

Spatial sensitivity measurements of a prototype GIC, as described above, were made with a 6 MV narrow (1 cm×1 cm) beam along the slope of the ion chamber. The magnitude of the response variation was found to be in agreement with the theoretically expected values (based on the variation of air volume along the length), with some deviation at the wider end of the chamber, which is discussed further below in relation to FIG. 7. This deviation is mainly due to the lack of lateral electronic equilibrium and also partially due to lower ion collection efficiency. However, a GIC can be designed to compensate for this relatively lower sensitivity at the edges by adding extra separation (more ionizing volume) between the electrode plates around the chamber edges (i.e. a non-linear increase in the gradient at the edge of the chamber can be used), or the ion chamber can be made slightly larger than the required dimension so that only the linear (monotonic) part of the sensitivity will be utilized in the AIMS.

Some initial tests have been performed to assess the effectiveness of the prototype GIC in determining a shift of a radiation field segment. A simple rectangular field defined by the X and Y jaws and an IMRT field defined by dynamic MLC segments was used. The results of these tests were found to be within approximately 1% of the expected value, as shown in Tables 2 and Table 3. In particular, Table 2 shows the measured and expected response of the prototype GIC to a static 10 cm×10 cm field at various off-axis distances, simulating corresponding shifts. All readings are normalized to the 0 cm offset reading. Table 3 shows the measured and expected response of the prototype GIC to a typical prostate patient IMRT field at various off-axis distances, simulating corresponding shifts. All readings are normalized to the 0 cm offset reading.

TABLE 2

Rectangular static field test on the prototype GIC
Static Field, 10 cm × 10 cm

| Off-Axis Position (cm) | Measured GIC Response | Expected GIC Response | Difference |
| --- | --- | --- | --- |
| −2 | 107.2 | 107.9 | −0.65% |
| −1 | 103.7 | 103.5 | 0.19% |
| 0 | 100.0 | 100.0 | 0.00% |

TABLE 2-continued

Rectangular static field test on the prototype GIC
Static Field, 10 cm × 10 cm

| Off-Axis Position (cm) | Measured GIC Response | Expected GIC Response | Difference |
|---|---|---|---|
| 1 | 94.7 | 95.3 | −0.63% |
| 2 | 90.5 | 90.3 | 0.22% |

TABLE 3

Measured and expected response of the prototype
GIC to a typical prostate patient IMRT field
IMRT Field

| Off-Axis Position (cm) | Measured GIC Response | Expected GIC Response | Difference |
|---|---|---|---|
| −1 | 103.3 | 103.5 | −0.21% |
| 0 | 100.0 | 100.0 | 0.00% |
| 2 | 91.3 | 90.3 | 1.11% |

The calculation parameters in equation 3 were experimentally derived for a 6 MV beam for Varian EX and Elekta Synergy-S linear accelerators with specified mounting geometry and MLC configuration. The relative chamber response function $\sigma(x,y)$ was obtained by mapping the signal to small ($1 \times 1$ cm$^2$) MLC-defined beamlets. The relative transmission factor of the MLC assembly, $T(x,y)$, was measured by digitizing a radiographic film exposed to the closed MLC transmission pattern with a fixed jaw size. The effect of the beam flatness is also included in these measurements. The relative output factor $ROF(X,Y)$ was measured using a diode with a copper-graphite buildup cap. To test the overall IQM system, first a set of square fields, defined by the MLC assembly 16 both centered and off-centered around the collimator axis of rotation were measured and calculated using the IQM calculation module 18. The results were compared and some parameters including the magnitude of the average MLC transmission and light-radiation field offset values were adjusted to refine the calculation model. Subsequently, tests were performed using standard as well as IMRT treatment fields.

Figure 6:
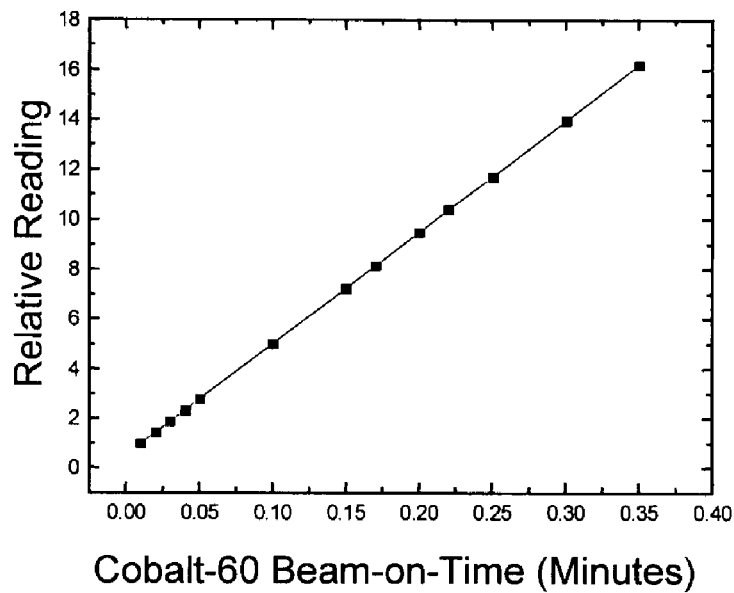
FIG. 6 is a plot of dose linearity of the AIMS with a Co-60 beam.

The reproducibility and linearity of the GIC response was investigated using a Co-60 teletherapy source as well as with linear accelerator beams. The signal reproducibility for a fixed beam was found to be within ±0.06% (1 standard deviation, N=50), while for an IMRT beam (prostate treatment field) the reproducibility was within ±0.1%. The GIC response was found to be highly linear as a function of the Beam-on-time for the Co-60 beams as well as for the linear accelerator beam, as illustrated in FIG. 6.

With the presence of the prototype GIC at the level of the shielding tray, the beam attenuation for 6 and 18 MV beams were found to be approximately 7% and 6% respectively, while the surface dose for a 6 MV radiation beam was found to have increased by only 1% and there was no increase in surface dose for an 18 MV radiation beam. Beam symmetry and flatness were not affected due to the prototype GIC. The effect of patient backscatter on the GIC signal was found to be negligible for the minimum treatment distance.

Figure 7:
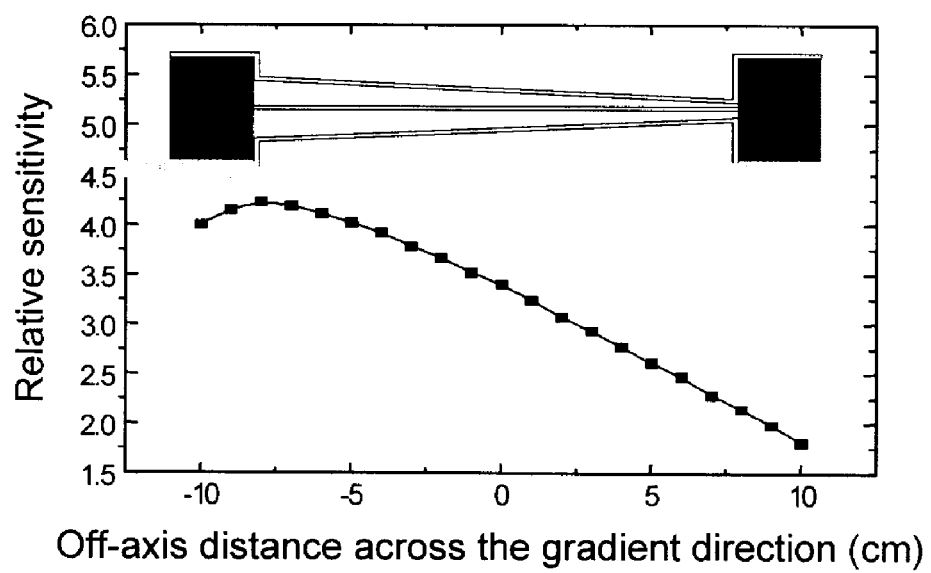
FIG. 7 is a plot showing spatial response of the GIC along the direction of MLC motion for the AIMS.

FIG. 7 shows the GIC response function through the midline of the gradient plane of the ion chamber along the direction of MLC motion (at y=0). The response plot shows a decrease in response at the thicker end of the chamber, which is mainly due to the loss of lateral electronic equilibrium at the edge of the wider separation of the chamber electrodes.

Figure 8:
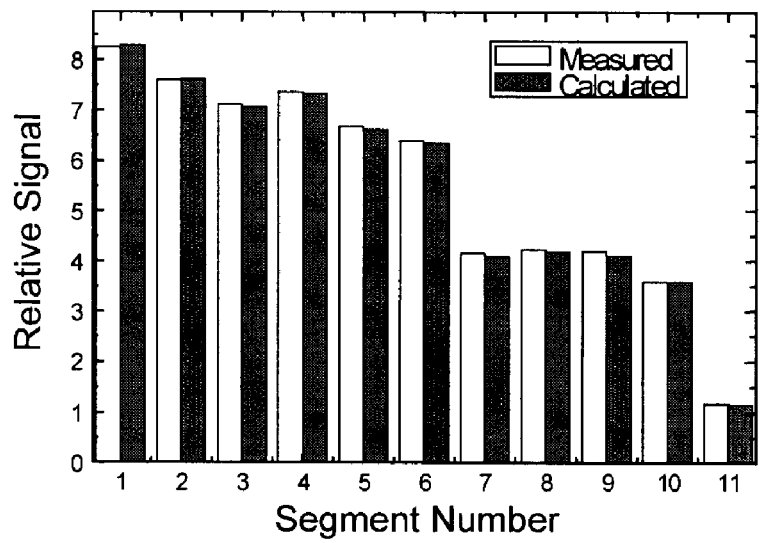
FIG. 8 is a plot showing a comparison between measured and calculated values for each segment of an IMRT field.

FIG. 8 shows measured and calculated results for each segment of a typical prostate IMRT field. For this test, each segment was individually delivered as a static 50 MU field in order to avoid the influence of dynamic delivery errors, which may be present in some delivery modes. The results show the agreement to be within 3%.

Figure 9:
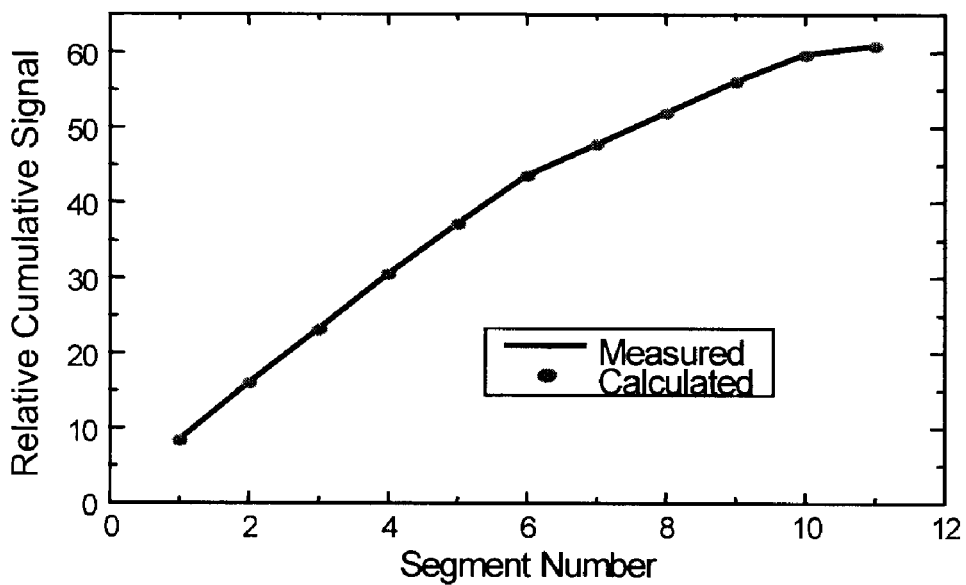
FIG. 9 is a plot of cumulative signal for an entire field.

The cumulative signal of a typical IMRT field is shown in FIG. 9, demonstrating how the GIC signal can be monitored dynamically during patient treatment. The line represents the measured GIC signal while the circles show the calculated values. A deviation of the measured signal from the calculated value by a predetermined tolerance indicates an error in the field delivery and the beam can be terminated (this is discussed in more detail below).

Figure 10:
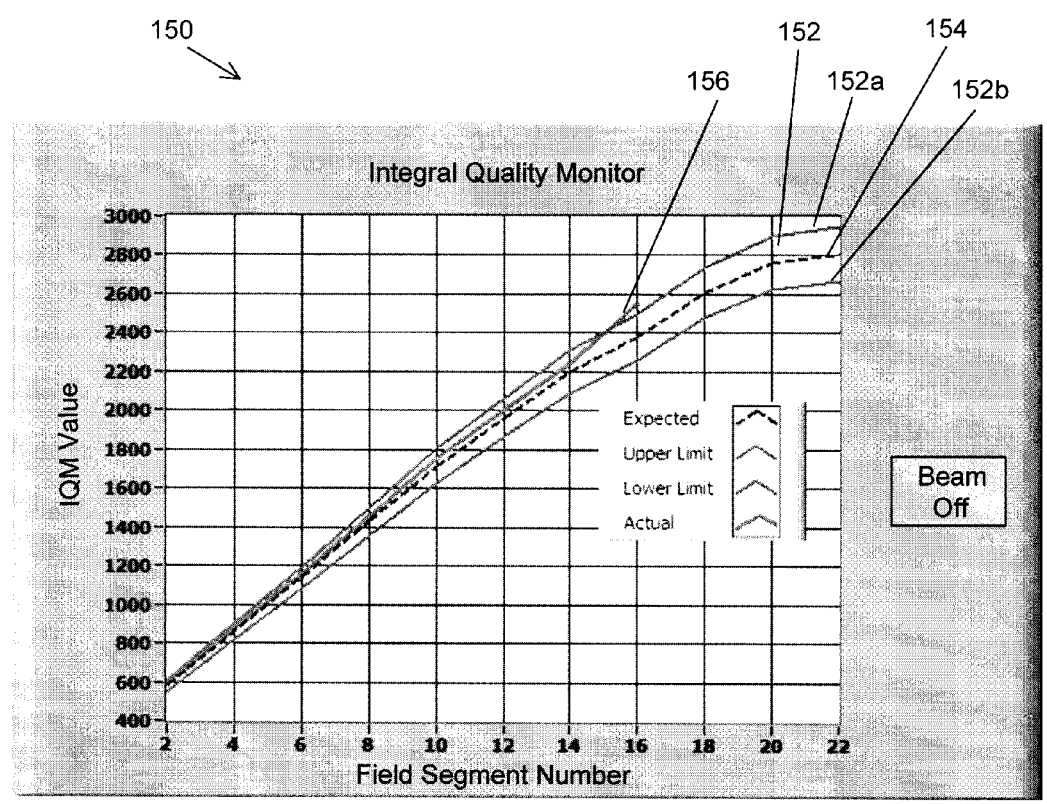
FIG. 10 is a plot illustrating a fluence delivery tolerance tunnel.

The QA of complex treatments used in modern radiation therapy techniques relies on redundant checks. The IQM system described herein can provide an audible alarm and beam interruption, as well as a real-time visual display representing the actual dose delivery to provide useful feedback to a radiation therapist that is using the radiation treatment and IQM systems. The proposed user interface provides a visual display of the expected and actual AIMS signal data showing real-time treatment delivery progress. An example of such a visual display 150 is shown in FIG. 10 illustrating a fluence delivery tolerance tunnel 152. An expected signal trajectory 154 is shown within the upper 152a and lower limits 152b of the tolerance tunnel 152, and the actual signal trajectory 156 is shown for data presentation to the user. The actual signal trajectory 156 and tolerance tunnel 152 are actually graphical displays of real-time cumulative signals from the AIMS and the corresponding tolerance envelope (e.g. ±3% of the expected cumulative signal trajectory 154) respectively. A comprehensive database may be provided to store the expected and actual delivered signal for each patient's record. This database may be linked to the main patient R&V system 12.

The tolerance limits for the tolerance tunnel 152 can be determined using a comprehensive set of test IMRT fields. A beam interrupt interlock for detected out of tolerance dose delivery is interfaced to the radiation source 14 through the existing interlock inputs provided for customer use by most manufacturers. Accordingly, during the actual treatment delivery, when the actual signal trajectory 156 crosses the upper and lower limits 152a and 152b of the tolerance tunnel 152, the IQM system can automatically disable the treatment machine using the beam interrupt interlock and may also trip an audible alarm. Alternatively, the user who is monitoring the visual display 150 can activate the beam interrupt interlock in the event of an error that results in the IQM signal drifting outside of the defined signal trajectory tunnel to terminate the radiation beam.

The user interface of the IQM system requires minimal interaction. The software has the ability to monitor the interface of the R&V system 12 and, if available, automatically extract the patient's name, ID and field name. If the patient information is not available from the interface of the R&V system 12, the treatment therapist can enter the information manually via the user interface of the IQM system. Using this information, the IQM system retrieves the expected IQM data and other treatment parameters from the IQM database (not shown). The pre-calculated signal trajectory and tolerance tunnel can be loaded and graphically displayed as shown in FIG. 10.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. For instance, certain calculations can be performed by either the processor 110 or the IQM console 24. Furthermore, this description is not to be considered as limiting the scope of these embodiments in any way, but rather as merely describing the implementation of these various embodiments. Accordingly, it should be understood that this application is intended to cover any variations, uses, or adaptations of the described embodiments following, in general, the principles outlined herein and including such departures from the teachings herein that come within known or customary practice within the art to which the teachings herein pertain and as follows in the scope of the appended claims.

The invention claimed is:

1. An area integrated fluence monitoring sensor for measuring a radiation dose from an ionizing radiation beam, wherein the sensor comprises:
    at least one Gradient Ion Chamber (GIC) comprising:
        an ion chamber having a volume gradient across a length or width thereof;
        a pair of polarizing electrodes defining upper and lower portions of the ion chamber and providing a portion of a housing for the at least one GIC, the pair of polarizing electrodes being oriented with respect to one another to provide the volume gradient;
        a gas or liquid located within the ion chamber; and
        an electrode to detect ions generated within the gas or liquid when the at least one GIC is subjected to the ionizing radiation beam, the electrode to detect ions being a collector plate disposed between the pair of polarizing electrodes,
wherein the ion chamber has a surface area larger than a cross-sectional area of the ionizing radiation beam at the at least one GIC and the sensor encodes a location and amount of ionizing radiation provided by the radiation beam at the at least one GIC.

2. The sensor as claimed in claim 1, wherein the volume gradient has a shape that monotonically increases in a given direction.

3. The sensor as claimed in claim 2, wherein the ion chamber is defined by electrodes and sidewalls that collectively provide a wedge shape.

4. The sensor as claimed in claim 1, wherein the at least one GIC further comprises:
    a pair of insulator regions separating end portions of the polarizing electrodes from one another at opposite ends of the ion chamber; and
    a pair of guard electrodes located within the insulating portions and configured to reduce the effect of leakage current on radiation dose measurement.

5. The sensor as claimed in claim 4, wherein each of the ends of the collector plate are located within one of the guard electrodes and the sensor further comprising an additional pair of insulator regions located within the guard electrodes to insulate the collector electrode from the guard electrodes.

6. The sensor as claimed in claim 4, wherein, during use, the pair of polarizing electrodes are maintained at a potential difference in the range of 300 to 500 Volts.

7. The sensor as claimed in claim 1, wherein the gas is air.

8. The sensor as claimed in claim 1, wherein the ion chamber is at room pressure.

9. The sensor as claimed in claim 1, wherein the sensor further comprises a temperature sensor for performing temperature compensation on the radiation dose measurement.

10. The sensor as claimed in claim 1, wherein the ion chamber is pressurized.

11. The sensor as claimed in claim 10, wherein the sensor further comprises a pressure sensor for performing pressure compensation on the radiation therapy dose measurement.

12. The sensor as claimed in claim 1, wherein the sensor comprises first and second GICs, the first GIC having a first ion chamber with a first volume gradient and the second GIC having a second ion chamber with a second volume gradient, wherein the second volume gradient is perpendicular to the first volume gradient.

13. The sensor as claimed in claim 1, wherein the sensor comprises first and second GICs, the first GIC having a first ion chamber with a first volume gradient and the second GIC having a second ion chamber with a second volume gradient, wherein the second volume gradient is parallel to and in an opposite direction with respect to the first volume gradient.

14. The sensor as claimed in claim 13, wherein the sensor further comprises third and fourth GICs, the third GIC having a third ion chamber with a third volume gradient and the fourth GIC having a fourth ion chamber with a fourth volume gradient, wherein the fourth volume gradient is parallel to and in an opposite direction with respect to the third volume gradient and the first and second volume gradients are orthogonal with respect to the third and fourth volume gradients.

15. The sensor as claimed in claim 1, wherein the volume gradient is characterized by a non-linear separation between polarizing electrodes.

16. The sensor as claimed in claim 1, wherein the ion chamber has a uniform gradient in one direction and a staircase-type gradient in an orthogonal direction.

17. The sensor as claimed in claim 1, wherein the volume gradient has a magnitude selected to achieve a desired spatial sensitivity gradient.

18. The sensor as claimed in claim 1, wherein the sensor comprises multiple GICs to provide a stacked gradient chamber.

19. An Integral Quality Monitoring (IQM) system for measuring a radiation dose provided by a radiation treatment system, the radiation treatment system establishing treatment parameters and including a radiation source for generating radiation therapy according to the treatment parameters, wherein the IQM system comprises:
    an Area Integrated Fluence Monitoring Sensor (AIMS) positioned between the radiation source and a patient location, the AIMS comprising at least one Gradient Ion Chamber (GIC) comprising an ion chamber having a volume gradient and a gas or liquid, the at least one GIC being configured to provide a GIC signal containing information on radiation dose and location of the radiation dose based on ions generated within the ion chamber when subjected to an ionizing radiation beam,
    an electrometer coupled to the AIMS for reading the GIC signal and providing measured AIMS signal data; and
    an IQM calculation module configured to predict expected AIMS signal data based on the treatment parameters and the configuration of the radiation source,
wherein the IQM system is configured to generate actual AIMS signal data from the measured AIMS signal data and compare the expected AIMS signal data with the actual AIMS signal data to monitor the characteristics of the radiation dose.

20. The IQM system as claimed in claim 19, wherein the radiation source further comprises an Multileaf Collimator (MLC) assembly to shape the output of the radiation source and wherein the GIC is positioned between the MLC assembly and a location where a patient is situated during radiation therapy.

21. The IQM system as claimed in claim 20, wherein the IQM calculation module is configured to predict the expected AIMS signal data based on a model that includes a primary beam component that is radiated through a first area defined by the aperture formed by the MLC assembly and a leakage component radiated through a second area defined by jaws of the radiation source minus the first area.

22. The IQM system as claimed in claim 21, wherein the IQM calculation module is configured to predict the expected AIMS signal data according to $$S = MU \cdot K \cdot ROF(X,Y)\left[\int_{A_1} F(x,y)\sigma(x,y)dxdy + \int_{A-A_1} T(x,y)F(x,y)\sigma(x,y)dxdy\right]$$

where S is a total integrated signal produced by the at least one GIC, A is the area enclosed by the jaws of the MLC assembly, $A_1$ is the area created by the aperture of the MLC assembly, MU is a scalar dose delivered in Monitor Units, K is a constant of proportionality, ROF(X,Y) is a field-size dependent relative output factor, F(x,y) is a beam fluence produced by the linac (over Area $A_1$), σ(x,y) is a chamber response function, and T(x,y) is an MLC transmission and leakage factor through the leaves of the MLC assembly (over Area A-$A_1$).

23. The IQM system as claimed in claim 19, wherein the AIMS comprises two or more GICs with ion chambers positioned to provide a multidirectional volume gradient, wherein the volume gradients of the ion chambers are in an orthogonal or in a parallel and opposite orientation with respect to one another.

24. The IQM system as claimed in claim 19, wherein the electrometer is a wide dynamic range electrometer comprising two electrometers in a switchable dual configuration and a processor, wherein the processor is configured to switch between the electrometers to prevent saturation of the electrometers such that one of the electrometers is integrating the GIC signal and the other electrometer is in reset mode.

25. The IQM system as claimed in claim 24, wherein the processor is configured to apply a gain correction factor to the output of the electrometers and to cumulatively add the outputs of the electrometers when switching between the electrometers while the radiation source is operating according to the treatment parameters.

26. The IQM system as claimed in claim 25, wherein the outputs from the electrometers are re-scaled based on actual delivered centi-Monitor Unit (cMU) if the radiation source provides a cMU count.

27. The IQM system as claimed in claim 24, wherein one of the electrometers comprises:
an integrator configured to integrate the GIC signal;
an analog to digital converter configured to digitize the integrated GIC signal; and
a logic gate configured to indicate a near saturation condition for of the integrator.

28. The IQM system as claimed in claim 19, wherein the IQM system is configured to provide radiation fluence measurements in real-time.

29. The IQM system as claimed in claim 19, wherein the IQM system further comprises data storage means to store measured and calculated radiation doses for given radiation treatment protocols.

30. A method for radiation dose measurement for a radiation treatment system, the radiation treatment system establishing treatment parameters and including a radiation source for generating a radiation beam according to the treatment parameters, wherein the method comprises:
positioning an Area Integrated Fluence Monitoring Sensor (AIMS) between the radiation source and a patient location, the AIMS including at least one Gradient Ion Chamber (GIC) comprising an ion chamber having a volume gradient and a gas or liquid;
predicting expected AIMS signal data based on the treatment parameters, the configuration of the radiation source and the AIMS;
operating the radiation source;
measuring AIMS signal data from the at least one GIC while the at least one GIC is subject to ionizing radiation;
generating actual AIMS signal data from the measured AIMS signal data and comparing the actual AIMS signal data with the expected AIMS signal data; and
detecting errors in the treatment parameters if the difference between the actual AIMS signal data and the expected AIMS signal data is not within tolerance limits.

31. The method as claimed in claim 30, wherein the method is performed before, during or after radiation treatment.

32. The method as claimed in claim 30, wherein an indication is provided to a user of the radiation treatment system when the difference between the actual AIMS signal data and the expected AIMS signal data is not within the tolerance limits.

33. The method as claimed in claim 30, wherein the radiation treatment system is based on standard radiation therapy modes, an Intensity Modulated Radiation Therapy (IMRT) and/or an Image Guide Adaptive Radiotherapy (IGART).

34. The method as claimed in claim 30, wherein the method further comprises providing the radiation source with a Multileaf Collimator (MLC) assembly to shape the output of the radiation source and positioning the AIMS between the MLC assembly and the patient location.

35. The method as claimed in claim 34, wherein predicting the expected AIMS signal data is based on using a model that includes a primary beam component that is radiated through a first area defined by the aperture formed by the MLC assembly and a leakage component radiated through a second area defined by jaws of the radiation source minus the first area.

36. The method as claimed in claim 35, wherein predicting the expected AIMS signal data is done according to $$S = MU \cdot K \cdot ROF(X,Y)\left[\int_{A_1} F(x,y)\sigma(x,y)dxdy + \int_{A-A_1} T(x,y)F(x,y)\sigma(x,y)dxdy\right]$$

where S is a total integrated signal produced by the at least one GIC, A is the area enclosed by the jaws of the MLC assembly, $A_1$ is the area created by the aperture of the MLC assembly, MU is a scalar dose delivered in Monitor Units, K is a constant of proportionality, ROF(X,Y) is a field-size dependent relative output factor, F(x,y) is a beam fluence produced by the linac (over Area $A_1$), σ(x,y) is a chamber response function, and T(x,y) is an MLC transmission and leakage factor through the leaves of the MLC assembly (over Area $A-A_1$).

37. The method as claimed in claim 30, wherein the method further comprises providing the AIMS with two or more GICs with ion chambers positioned to provide a multidirectional volume gradient in which the volume gradients of the ion chambers are in an orthogonal or in a parallel and opposite orientation with respect to one another.

38. The method as claimed in claim 30, wherein the measuring is performed using a wide dynamic range electrometer comprising two electrometers in a switchable dual configuration and the method comprises switching between the electrometers to prevent saturation of the electrometers such that one of the electrometers is integrating the GIC signal and the other electrometer is in reset mode.

39. The method as claimed in claim 38, wherein the method further comprises applying a gain correction factor to the output of the electrometers and cumulatively adding the outputs of the electrometers when switching between the electrometers while the radiation source is operating according to the treatment parameters.

40. The method as claimed in claim 39, wherein the method further comprises re-scaling the outputs from the electrometers based on actual delivered centi-Monitor Unit (cMU) if the radiation source provides a cMU count.

41. The method as claimed in claim 30, wherein the method further comprises storing measured and calculated radiation doses for given radiation treatment protocols.

42. The method as claimed in claim 30, wherein the method further comprises providing multiple GICs to provide a stacked gradient chamber.

43. The method as claimed in claim 30, wherein the method further comprises stopping treatment if the difference between the actual AIMS signal data and the expected AIMS signal data is not within tolerance limits.

44. The method as claimed in claim 30, wherein the method further comprises providing a user interface with a graphical depiction of the expected and actual AIMS signal data to allow a user to visually monitor the operation of the radiation treatment system.

45. An area integrated fluence monitoring sensor for measuring a radiation dose from an ionizing radiation beam, wherein the sensor comprises:
a first Gradient Ion Chamber (GIC) comprising:
a first ion chamber having a first volume gradient across a length or width thereof;
a first gas or first liquid located within the first ion chamber; and
a first electrode to detect ions generated within the first gas or first liquid when the first GIC is subjected to the ionizing radiation beam; and
a second GIC comprising:
a second ion chamber having a second volume gradient across a length or width thereof;
a second gas or second liquid located within the second ion chamber; and
a second electrode to detect ions generated within the second gas or second liquid when the second GIC is subjected to the ionizing radiation beam;
wherein the first and second ion chambers have a surface area larger than a cross-sectional area of the ionizing radiation beam at the first and second GICs, the second volume gradient is parallel to and in an opposite direction with respect to the first volume gradient and the sensor encodes a location and amount of ionizing radiation provided by the radiation beam at the first and second GICs.

46. The sensor as claimed in claim 45, wherein a given GIC further comprises:
a pair of polarizing electrodes defining upper and lower portions of the ion chamber and a portion of a housing of the given GIC, the pair of polarizing electrodes being oriented with respect to one another to provide the volume gradient of the given GIC;
a pair of insulator regions separating end portions of the polarizing electrodes from one another at opposite ends of the ion chamber of the given GIC; and
a pair of guard electrodes located within the insulating portions and configured to reduce the effect of leakage current on radiation dose measurement.

47. The sensor as claimed in claim 46, wherein the first electrode that detects ions is a collector plate disposed between the pair of polarizing electrodes, each of the ends of the collector plate being located within one of the guard electrodes and the given GIC further comprising an additional pair of insulator regions located within the guard electrodes to insulate the collector electrode from the guard electrodes of the given GIC.

48. The sensor as claimed in claim 45, wherein a given GIC further comprises:
a polarizing electrode defining an upper or lower portion of the ion chamber and a portion of a housing for the given GIC;
a collector plate disposed across from the polarizing electrode to define the volume gradient of the given GIC;
insulator regions separating end portions of the polarizing electrode from the collector plate at opposite ends of the ion chamber of the given GIC; and
a pair of guard electrodes located within the insulating portions and configured to reduce the effect of leakage current on radiation dose measurement.

49. An area integrated fluence monitoring sensor for measuring a radiation dose from an ionizing radiation beam, wherein the sensor comprises:
a single Gradient Ion Chamber (GIC) comprising:
an ion chamber having a volume gradient across a length or width thereof;
a gas or liquid located within the ion chamber; and
an electrode to detect ions generated within the gas or liquid when the single GIC is subjected to the ionizing radiation beam,
wherein the ion chamber has a surface area larger than a cross-sectional area of the ionizing radiation beam at the single GIC, a magnitude for the volume gradient is selected to achieve a desired spatial sensitivity and the sensor encodes a location and amount of ionizing radiation provided by the radiation beam at the single GIC through a single signal.

50. The sensor as claimed in claim 49, wherein the single GIC further comprises:
a pair of polarizing electrodes defining upper and lower portions of the ion chamber and providing a portion of a housing for the single GIC, the pair of polarizing electrodes being oriented with respect to one another to provide the volume gradient;
a pair of insulator regions separating end portions of the polarizing electrodes from one another at opposite ends of the ion chamber; and
a pair of guard electrodes located within the insulating portions and configured to reduce the effect of leakage current on radiation dose measurement.

51. The sensor as claimed in claim 50, wherein the electrode that detects ions is a collector plate disposed between the pair of polarizing electrodes, each of the ends of the collector plate being located within one of the guard electrodes and the sensor further comprising an additional pair of insulator regions located within the guard electrodes to insulate the collector electrode from the guard electrodes.

52. The sensor as claimed in claim 49, wherein the single GIC further comprises:
   a polarizing electrode defining an upper or lower portion of the ion chamber and providing a portion of a housing for the single GIC;
   a collector plate disposed across from the polarizing electrode to define the volume gradient;
   insulator regions separating end portions of the polarizing electrode from the collector plate at opposite ends of the ion chamber; and
   a pair of guard electrodes located within the insulating portions and configured to reduce the effect of leakage current on radiation dose measurement.

53. The sensor as claimed in claim 49, wherein the single GIC further comprises electrode plates defining the ion chamber and the electrode plates are configured to provide extra separation around edges of the ion chamber to compensate for lower sensitivity at the edges of the single GIC.

* * * * *